US012369849B2

(12) United States Patent
Zhou

(10) Patent No.: US 12,369,849 B2
(45) Date of Patent: Jul. 29, 2025

(54) MULTI-PLANE SLEEP MONITORING ENDOSCOPE

(71) Applicant: Xing Zhou, Guangzhou (CN)

(72) Inventor: Xing Zhou, Guangzhou (CN)

(*) Notice: Subject to any disclaimer, the term of this patent is extended or adjusted under 35 U.S.C. 154(b) by 582 days.

(21) Appl. No.: 17/573,493

(22) Filed: Jan. 11, 2022

(65) Prior Publication Data

US 2022/0151550 A1     May 19, 2022

Related U.S. Application Data

(63) Continuation of application No. PCT/CN2020/091291, filed on May 20, 2020.

(30) Foreign Application Priority Data

Aug. 8, 2019    (CN) .......................... 201910731849.9

(51) Int. Cl.
*A61B 5/00*      (2006.01)
*A61B 1/00*      (2006.01)
(Continued)

(52) U.S. Cl.
CPC ........ *A61B 5/4818* (2013.01); *A61B 1/00016* (2013.01); *A61B 1/00045* (2013.01);
(Continued)

(58) Field of Classification Search
None
See application file for complete search history.

(56) References Cited

U.S. PATENT DOCUMENTS 4,343,300 A * 8/1982 Hattori ............... A61B 1/00006
                                                        396/17
5,174,287 A * 12/1992 Kallok ................. A61N 1/3601
                                                        607/42
(Continued)

FOREIGN PATENT DOCUMENTS

CN        102149312 A      8/2011
CN        104434012 A      3/2015
(Continued)

OTHER PUBLICATIONS

Zhou, Xing, International Search Report, PCT/CN2020/091291, Aug. 19, 2020, 5 pgs.
(Continued)

*Primary Examiner* — John P Leubecker
(74) *Attorney, Agent, or Firm* — Morgan, Lewis & Bockius LLP

(57) ABSTRACT

A multi-plane sleep monitoring endoscope includes an observation system, a data processing and outputting system, a lighting system, a display system, a circuit, a shell, and a power system. The observation system is a photographing system and includes two sets of imaging systems; distal ends of the imaging systems form observation ends, and the observation ends are not on the same horizontal plane. A positioning system can adjust a distance L between the horizontal planes where the observation ends are located and spatial states of the observation ends. The at least two sets of imaging systems can simultaneously perform observation and display on the display system. The multi-plane sleep monitoring endoscope can simultaneously monitor different planes in the sleep process of an obstructive sleep apnea/hypopnea syndrome patient, particularly suitable for simultaneously monitoring the velopharyngeal plane and the (Continued)

glossopharyngeal plane, and is safe and efficient in the clinical use process.

18 Claims, 19 Drawing Sheets

(51) Int. Cl.
    *A61B 1/005*     (2006.01)
    *A61B 1/018*     (2006.01)
    *A61B 1/05*     (2006.01)
    *A61B 1/06*     (2006.01)
    *A61B 1/07*     (2006.01)
    *A61B 1/267*     (2006.01)

(52) U.S. Cl.
    CPC .............. *A61B 1/005* (2013.01); *A61B 1/018* (2013.01); *A61B 1/051* (2013.01); *A61B 1/0684* (2013.01); *A61B 1/07* (2013.01); *A61B 1/267* (2013.01); *A61B 2562/0247* (2013.01)

(56) References Cited

U.S. PATENT DOCUMENTS

| | | | | |
|---|---|---|---|---|
| 5,178,130 | A * | 1/1993 | Kaiya | A61B 1/042<br>348/E5.025 |
| 5,647,838 | A * | 7/1997 | Bloomer | H04N 13/341<br>348/E13.071 |
| 5,876,325 | A * | 3/1999 | Mizuno | A61B 34/37<br>600/117 |
| 6,066,090 | A * | 5/2000 | Yoon | A61B 17/3417<br>600/113 |
| 6,572,543 | B1 * | 6/2003 | Christopherson | A61B 5/03<br>607/42 |
| 7,318,802 | B2 * | 1/2008 | Suzuki | A61B 17/0469<br>606/139 |
| 7,662,089 | B2 * | 2/2010 | Okada | A61B 1/018<br>600/113 |
| 8,197,399 | B2 * | 6/2012 | Bayer | A61B 1/0625<br>600/113 |
| 8,764,632 | B2 | 7/2014 | Kezirian et al. | |
| 2002/0074463 | A1 * | 6/2002 | Nakamura | A61B 90/50<br>248/127 |
| 2003/0135091 | A1 * | 7/2003 | Nakazawa | A61B 1/313<br>600/101 |
| 2005/0038317 | A1 * | 2/2005 | Ratnakar | A61B 1/0623<br>600/101 |
| 2006/0149129 | A1 * | 7/2006 | Watts | A61B 1/0125<br>600/113 |
| 2007/0106113 | A1 * | 5/2007 | Ravo | A61B 1/00154<br>600/128 |
| 2007/0255100 | A1 * | 11/2007 | Barlow | A61B 1/00105<br>600/114 |
| 2008/0051629 | A1 * | 2/2008 | Sugiyama | A61B 1/018<br>600/114 |
| 2009/0082622 | A1 * | 3/2009 | Takekoshi | A61B 1/015<br>600/104 |
| 2009/0306528 | A1 * | 12/2009 | Curti | A61B 5/087<br>600/537 |
| 2010/0094376 | A1 * | 4/2010 | Penner | A61N 1/0517<br>607/42 |
| 2010/0261962 | A1 * | 10/2010 | Friedberg | A61B 1/00082<br>600/114 |
| 2011/0160530 | A1 * | 6/2011 | Ratnakar | A61B 1/04<br>600/109 |
| 2011/0251457 | A1 * | 10/2011 | Kezirian | A61B 1/00016<br>600/109 |
| 2012/0065470 | A1 * | 3/2012 | Olds | A61B 34/30<br>901/41 |
| 2012/0088963 | A1 * | 4/2012 | Yasunaga | A61B 1/3132<br>600/102 |
| 2015/0051449 | A1 * | 2/2015 | Qiu | A61B 5/0836<br>600/407 |
| 2016/0022118 | A1 * | 1/2016 | Dejima | A61B 17/3462<br>600/104 |
| 2018/0078115 | A1 * | 3/2018 | Gupta | A61B 1/06 |
| 2019/0008367 | A1 * | 1/2019 | Ishikawa | A61B 90/361 |
| 2019/0125170 | A1 * | 5/2019 | Yahagi | A61B 1/00154 |
| 2020/0022569 | A1 * | 1/2020 | Wake | A61B 1/015 |
| 2020/0154982 | A1 * | 5/2020 | Niwa | A61B 1/00126 |

FOREIGN PATENT DOCUMENTS

| | | |
|---|---|---|
| CN | 105078426 A | 11/2015 |
| CN | 105640485 A | 6/2016 |
| CN | 107713968 A | 2/2018 |
| CN | 110833379 A | 2/2020 |
| JP | 07250813 A * | 10/1995 |
| JP | 2009284956 A | 12/2009 |

OTHER PUBLICATIONS

Zhou, Xing, International Preliminary Report on Patentability and Written Opinion, PCT/CN2020/09129, Aug. 19, 2020, 14 pgs.
Zhou, Xing, European Search Report, EP20849133.2, Aug. 1, 2023, 8 pgs.

* cited by examiner

Sectional enlarged diagram of part A

Enlarged diagram of part B

Enlarged diagram of part D

Enlarged diagram of part E

Enlarged diagram of part G

Sectional diagram of part H

MULTI-PLANE SLEEP MONITORING ENDOSCOPE

CROSS-REFERENCE TO RELATED APPLICATIONS

This application is a continuation application of PCT Patent Application No. PCT/CN2020/091291, entitled "MULTI-PLANE SLEEP MONITORING ENDOSCOPE" filed on May 20, 2020, which claims priority to Chinese Patent Application No. 201910731849.9, entitled "MULTI-PLANE SLEEP MONITORING ENDOSCOPE" and filed with the China National Intellectual Property Administration on Aug. 8, 2019, both of which are incorporated herein by reference in their entirety.

TECHNICAL FIELD

The present application relates to a multi-plane sleep monitoring endoscope, and in particular to a multi-plane sleep monitoring endoscope used for treating sleep apnea syndrome and obstructive sleep apnea/hypopnea syndrome (hereinafter referred to as OSAHS).

BACKGROUND

The obstructive sleep apnea/hypopnea syndrome is a sleep disordered breathing disease with clinical features of snoring, apnea and hypopnea caused by collapse and obstruction of the soft tissues of the upper airway during sleep.

For the pathogenesis of the OSAHS, it is generally believed that there are multiple factors jointly causing the OSAHS. In addition to the stenosis of the anatomical structure of the upper airway, there is also an obstruction factor caused by collapse of the soft tissues since the dilator muscle that keeps the upper airway open during sleep relaxes. The obstructive site may be located in one or more planes such as the nasopharyngeal plane, the velopharyngeal plane, the glossopharyngeal plane, and the epiglottic plane.

The determination of the obstructive plane is the basis for selecting a correct treatment plan for the OSAHS, and the most direct and effective method for detecting the obstructive plane is to directly observe, through a medical endoscope, a site that may be obstructive during sleep. The OSAHS is a result of multiple factors. A patient often has obstructions on multiple planes during sleep. Therefore, it is necessary to detect the positions of the multiple planes at the same time. However, the current medical endoscopes are all single-set imaging systems, and only one plane can be detected at each time. Therefore, the current medical endoscope for sleep detection cannot fully confirm the obstructive sites of the patient at one time.

This patent application is a further improvement and perfection of the existing medical endoscope for sleep monitoring.

SUMMARY

A multi-plane sleep monitoring endoscope of the present application is designed with two or more sets of imaging systems through which different planes can be observed. A plurality of obstructive planes can be simultaneously monitored by one sleep monitoring. It is of great significance for confirming OSAHS obstructive planes.

The multi-plane sleep monitoring endoscope of the present application is characterized in that:

A. a multi-plane sleep monitoring endoscope 100 includes an observation system 1, a data processing and outputting system 2, a lighting system 3, a display system 4, a circuit 5, a shell 6, and a power system 8;
B. the observation system 1 is a photographing system 11; the photographing system 11 at least includes two sets of imaging systems 11-1; and
C. the data processing and outputting system 2 and the circuit 5 are mounted in the shell 6; and the observation system 1, the data processing and outputting system 2, the lighting system 3, and the display system 4 are connected to the power system 8 through the circuit 5.

The two or more sets of imaging systems 11-1 may simultaneously work in a sleep process and simultaneously monitor a plurality of parts to realize one-time monitoring of a plurality of planes. After being processed by the data processing and outputting system 2, data acquired by the imaging systems 11-1 may be output to the same display system 4 for displaying on split screens or may be output to different display systems 4 for separate displaying. In a monitoring process, the lighting system 3 can provide sufficient light for the imaging systems 11-1 to ensure an imaging effect during monitoring.

The imaging system 11-1 includes a lens 11-11, the data processing and outputting system 2, the circuit 5, and the power system 8; and data acquired by the lens 11-11 may be output to the display system 4 after being processed by the data processing and outputting system 2. As needed, the data acquired by the plurality of lenses 11-11 may be simultaneously output to one display system 4 for displaying on split screens, or may be output to different display systems 4 for separate displaying.

A distal end of the imaging system 11-1 forms an observation end 11-12; and the observation ends 11-12 of at least two imaging systems 11-1 are not on the same horizontal plane. Since obstructive planes are located on different horizontal planes, the observation ends 11-12 of two or more imaging systems 11-1 are not on the same horizontal plane, so as to realize simultaneous monitoring of different obstructive planes.

The photographing system 11 further includes a positioning system 11-2; and the positioning system 11-2 may position the observation end 11-12 of the imaging system 11-1. The observation end 11-12 of the imaging system can be spatially positioned through the positioning system 11-2, so that it is ensured that the observation end can be located at a suitable monitoring part and can well adapt to the individual differences of different patients. The positioning system 11-2 may be a manual positioning system or may be an automatically controlled positioning system. Those skilled in the art can design different positioning systems as needed without departing from the protection scope of the present application.

The positioning system 11-2 includes a monitored plane positioning mechanism 11-21 and a spatial state positioning mechanism 11-22. The monitored plane positioning mechanism 11-21 may adjust a horizontal height of the observation end 11-12 to ensure that the observation end 11-12 is located on an obstructive plane to be monitored. The spatial state positioning mechanism 11-22 can adjust a spatial state of the observation end 11-12 during observation to ensure that the observation end 11-12 can have a good observation field of view during monitoring of different parts.

A distance L between the planes where the observation ends 11-12 of the at least two imaging systems 11-1 are located may be adjusted through the monitored plane positioning mechanism 11-21. Due to the individual differences and physiological characteristics, distances between different patients and between different obstructive planes are clinically different, so that the distance L between the observation ends 11-12 can be adjusted to well adapt to the differences between different patients and between different observation planes.

The monitored plane positioning mechanism 11-21 adjusts, by means of a sliding chute, rotation around an axis, or a cam, the distance L between the planes where the observation ends 11-12 are located. The applicant only lists the above several distance adjusting methods here. In practical application, those skilled in the art can design different distance adjusting methods as needed without departing from the protection scope of the present application.

The spatial state positioning mechanism 11-22 can adjust the spatial state of the observation end 11-12. The spatial state positioning mechanism 11-22 can adjust different spatial position parameters such as radian and angle of the observation end 11-12 to ensure a good observation field of view in the monitoring process.

The imaging system 11-1 is a fiberoptic endoscope 1101. A distal end of an image guide fiber 11-13 of the fiberoptic endoscope 1101 forms the observation end 11-12 and is connected to the lens 11-11. The lighting system 3 provides illumination for the observation end 11-12 through a light guide fiber 32.

The imaging system 11-1 is an electronic endoscope 1102. A distal end of the lens 11-11 of the electronic endoscope 1102 forms the observation end 11-12; the data acquired by the lens 11-11 is output to the display system 4 after being processed by the data processing and outputting system 2; the lighting system 3 includes a light source 31 and the light guide fiber 32; the light guide fiber 32 guides illuminating light emitted by the light source 31 to the observation end 11-12 to provide illumination for the lens 11-11. In the method for guiding light by a fiber, the light source can be mounted at the rear, so that no heat is generated around the lens 11-11. It is very safe when this device is placed in a human body for a long time, and surrounding tissues will not be accidentally scalded.

The lighting system 3 is arranged around the lens 11-11 of the electronic endoscope 1102 to provide illumination for the lens 11-11. The lighting system 3 is directly arranged around the lens 11-11, so that the illumination effect is better.

The lighting system 3 is a light-emitting diode (LED) light source. Compared with an ordinary illumination light source, the LED light source has the characteristics of small volume, high light-emitting efficiency, high light directivity, and the like. Particularly in terms of safety, the LED light source has incomparable advantages to the ordinary light source. First of all, the LED light source is supplied with low-voltage direct current power, and a power supply voltage is only 6 to 24 V. Secondly, no mercury is added into the LED light source, which will not cause poisoning and other harm to the human body. In addition, more importantly, the LED light source is a cold light source, which will not seriously generate heat in a working process. The LED light source can be safely touched and will not cause accidental high-temperature scald to the human body.

For the electronic endoscope 1102, since the lens 11-11 is arranged at the distal end of the multi-plane sleep monitoring endoscope 100, the data acquired by the lens 11-11 can be transmitted through the small circuit 5, so except that the lens 11-11 has a certain size, other insertion parts of the multi-plane sleep monitoring endoscope 100 entering cavities of the human body can ensure a very small size.

Therefore, after the multi-plane sleep monitoring endoscope 100 is mounted, it has little impact on the sleep of the patient in the monitoring process.

The data may be output to the display system 4 in a wired or wireless manner after being processed by the data processing and outputting system 2. The data can be directly connected and output to the display system 4 in the wired manner such as through a universal serial bus (USB) cable, and can also be transmitted to the display system 4 in the wireless manner such as through Bluetooth, and WI-FI. The processed data can also be output to a storage device for storage and copying.

The display system 4 is a smart phone 41, a computer 42, a liquid crystal display 43, or a tablet computer 44.

The multi-plane sleep monitoring endoscope 100 is made of a medical material. Due to the good biological safety performance of the medical material, the monitoring process is safer and more reliable.

The observation system 1 is delivered through a flexible sheath 6-1. By the delivery process of the soft flexible sheath 6-1, a patient feels more comfortable.

The flexible sheath 6-1 includes at least two working channels 6-11, and channel outlet ends 6-11-1 of the working channels 6-11 are not on the same horizontal plane. The flexible sheath 6-1 includes a plurality of working channels 6-11, and a plurality of sets of the imaging systems 11-1 can be simultaneously placed in one flexible sheath 6-1; and the imaging systems 11-1 of the plurality of planes can be mounted in one delivery.

Further, the observation system 1 is provided with a pressure sensor 7 or a flow velocity sensor 9 near the observation end 11-12. The pressure sensor 7 can measure a pressure of a breathing air flow near the observation end 11-12, and the flow velocity sensor 9 can measure a flow rate of the breathing air flow near the observation end 11-12.

During clinical use, the observation system 1, the lighting system 3, the data display system 4, and the power system 8 of the multi-plane sleep monitoring endoscope of the present application are connected; the power system 8 is turned on; the observation system 1 and the lighting system 3 are activated; the observation system 1 starts to acquire data; and the data is transmitted, via the circuit 5, to the display system 4 for displaying after being processed by the data processing and outputting system 2. After the multi-plane sleep monitoring endoscope 100 is operated normally, insertion parts 1-1 of the observation system 1 respectively enter the upper respiratory tract along the nasal cavity and are delivered to different monitored planes. For example, the observation ends 11-12 are respectively delivered to the velopharyngeal plane and the glossopharyngeal plane; at the same time, the spatial positions of the observation ends 11-12 of all the imaging systems 11-1 are adjusted through the positioning system 11-2; and all the imaging systems 11-1 are locked to start sleep monitoring. A bracket 6-2 can fix the observation system 1 on a fixed object such as a sickbed to ensure that the observation ends 11-12 of the observation system 1 are located at set monitoring positions in the long-time sleep monitoring process.

The multi-plane sleep monitoring endoscope of the present application includes the observation system 1, the data processing and outputting system 2, the lighting system 3, the display system 4, the circuit 5, the shell 6, and the power system 8. The observation system 1 at least includes two sets of imaging systems 11-1; the distal ends of the imaging systems 11-1 form the observation ends 11-12; and the observation ends 11-12 of the imaging systems 11-1 are not on the same horizontal plane. The positioning system 11-2 can adjust the distance L between the horizontal planes where the observation ends 11-12 are located and the spatial states of the observation ends 11-12. The at least two sets of imaging systems 11-1 can simultaneously perform observation and display on the display system 4. The multi-plane sleep monitoring endoscope can simultaneously monitor different planes in the sleep process of an obstructive sleep apnea/hypopnea syndrome (OSAHS) patient, particularly suitable for simultaneously monitoring the velopharyngeal plane and the glossopharyngeal plane, and is safe and efficient in the clinical use process.

BRIEF DESCRIPTION OF THE DRAWINGS

FIG. 5C is a schematic structural diagram illustrating that the locking switch of the sliding chute type distance adjusting mechanism in FIG. 5A is on.

FIG. 5D is a front view illustrating that the locking switch of the sliding chute type distance adjusting mechanism in FIG. 5A is on.

In the foregoing figures:
1: observation system; 2: data processing and outputting system; 3: lighting system; 4: display system; 5: circuit; 6: shell; 7: pressure sensor; 8: power system; 9: flow velocity sensor; 100: multi-plane sleep monitoring endoscope of the present application.

1-1: insertion part of the multi-plane sleep monitoring endoscope of the present application.

11: photographing system; 11-1: imaging system; 11-11: lens; 11-12: observation end; 11-13: image guide fiber; 11-2: positioning system; 11-21: monitored plane positioning mechanism; 11-22: spatial state positioning mechanism; 11-23: body surface positioning mechanism; 11-21-1: locking switch; 11-21-2: sliding chute hole; 11-22-1: adjusting knob; 1101: fiberoptic endoscope; 1102: electronic endoscope.

31: light source; 32: light guide fiber.

41: smart phone; 42: computer; 43: liquid crystal display; 44: tablet computer.

6-1: flexible sheath; 6-11: working channel; 6-11-1: channel outlet end; 6-2: bracket.

DESCRIPTION OF EMBODIMENTS

Figure 1:
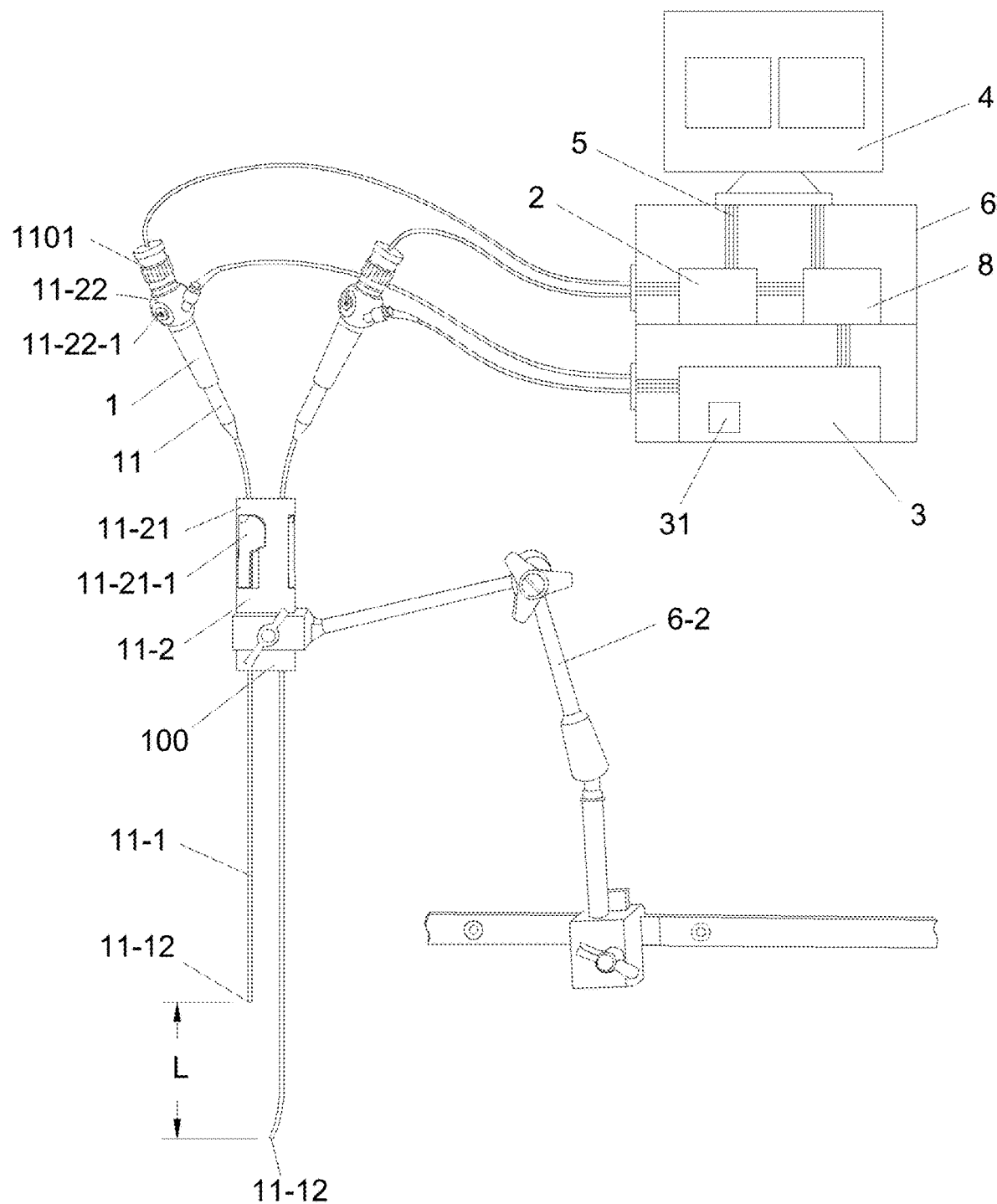
FIG. 1 is a schematic structural diagram of a multi-plane sleep monitoring endoscope of the present application including two fiberoptic endoscopes.

Embodiment 1: Multi-plane sleep monitoring endoscope of the present application including a fiberoptic endoscope Referring to FIG. 1, in this embodiment, a multi-plane sleep monitoring endoscope 100 includes an observation system 1, a data processing and outputting system 2, a lighting system 3, a display system 4, a circuit 5, a shell 6, and a power system 8.

Figure 5A:
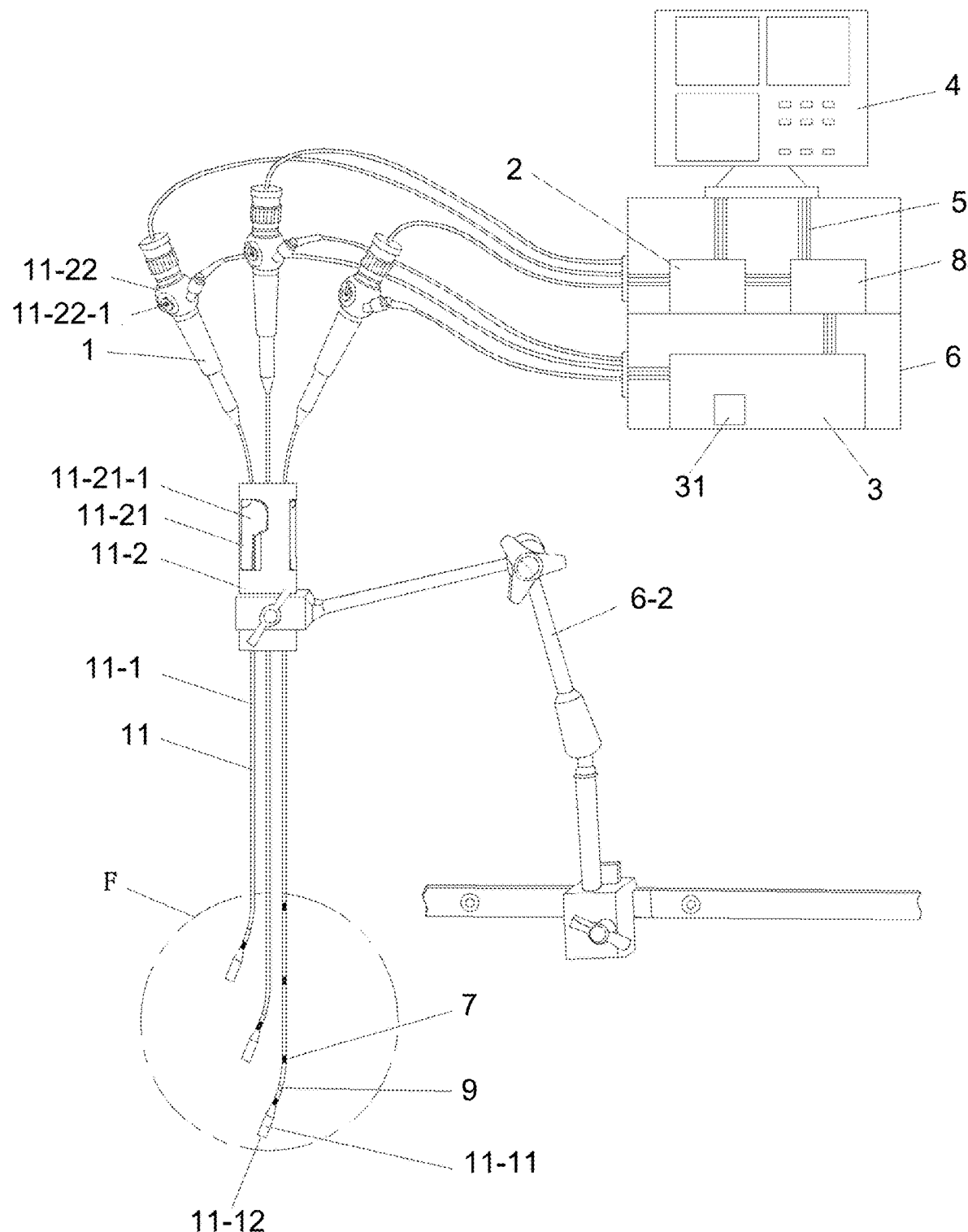
FIG. 5A is a schematic structural diagram of a multi-plane sleep monitoring endoscope of the present application including three electronic endoscopes.
Figure 5B:
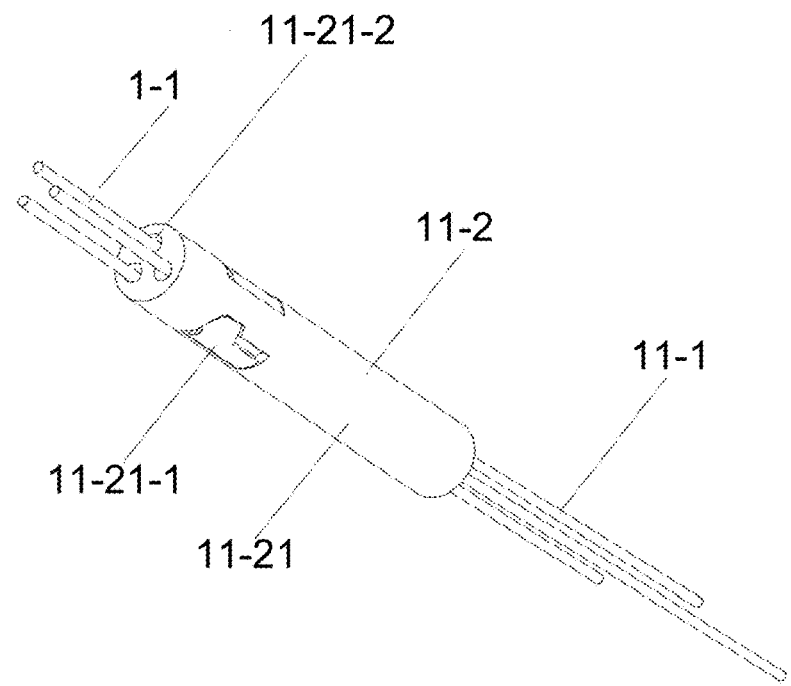
FIG. 5B is a schematic structural diagram illustrating that a locking switch of a sliding chute type distance adjusting mechanism in FIG. 5A is off.
Figure 5C:
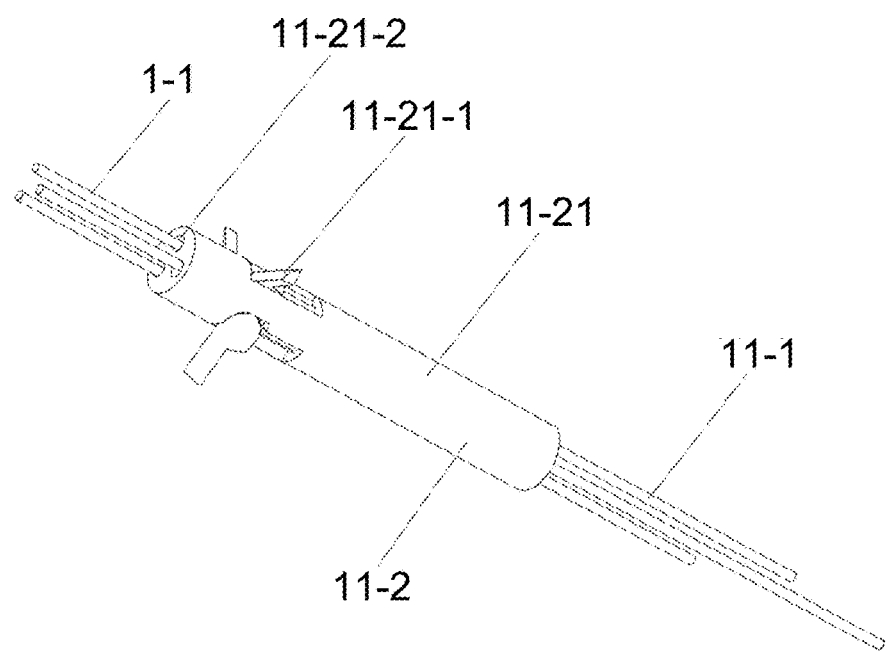
Figure 5D:
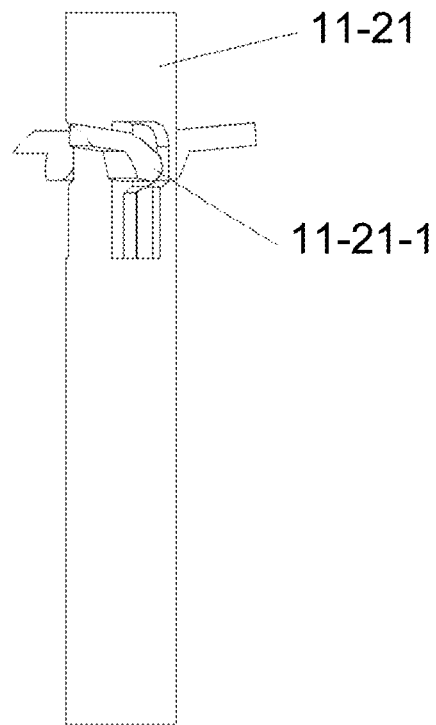
Figure 5E:
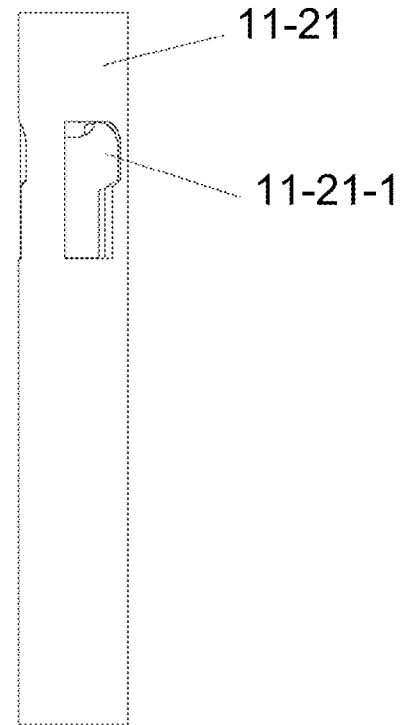
FIG. 5E is a front view illustrating that the locking switch of the sliding chute type distance adjusting mechanism in FIG. 5A is off.
Figure 5F:
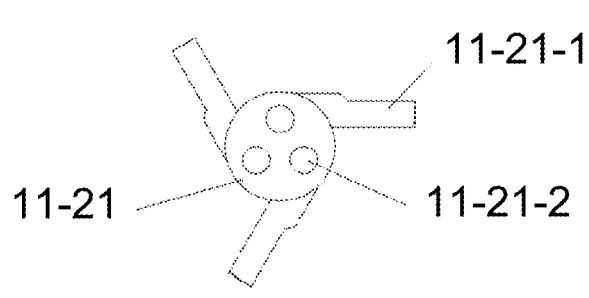
FIG. 5F is a top view of FIG. 5D.
Figure 5G:
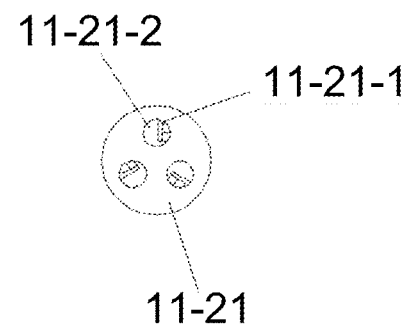
FIG. 5G is a top view of FIG. 5E.
Figure 6:
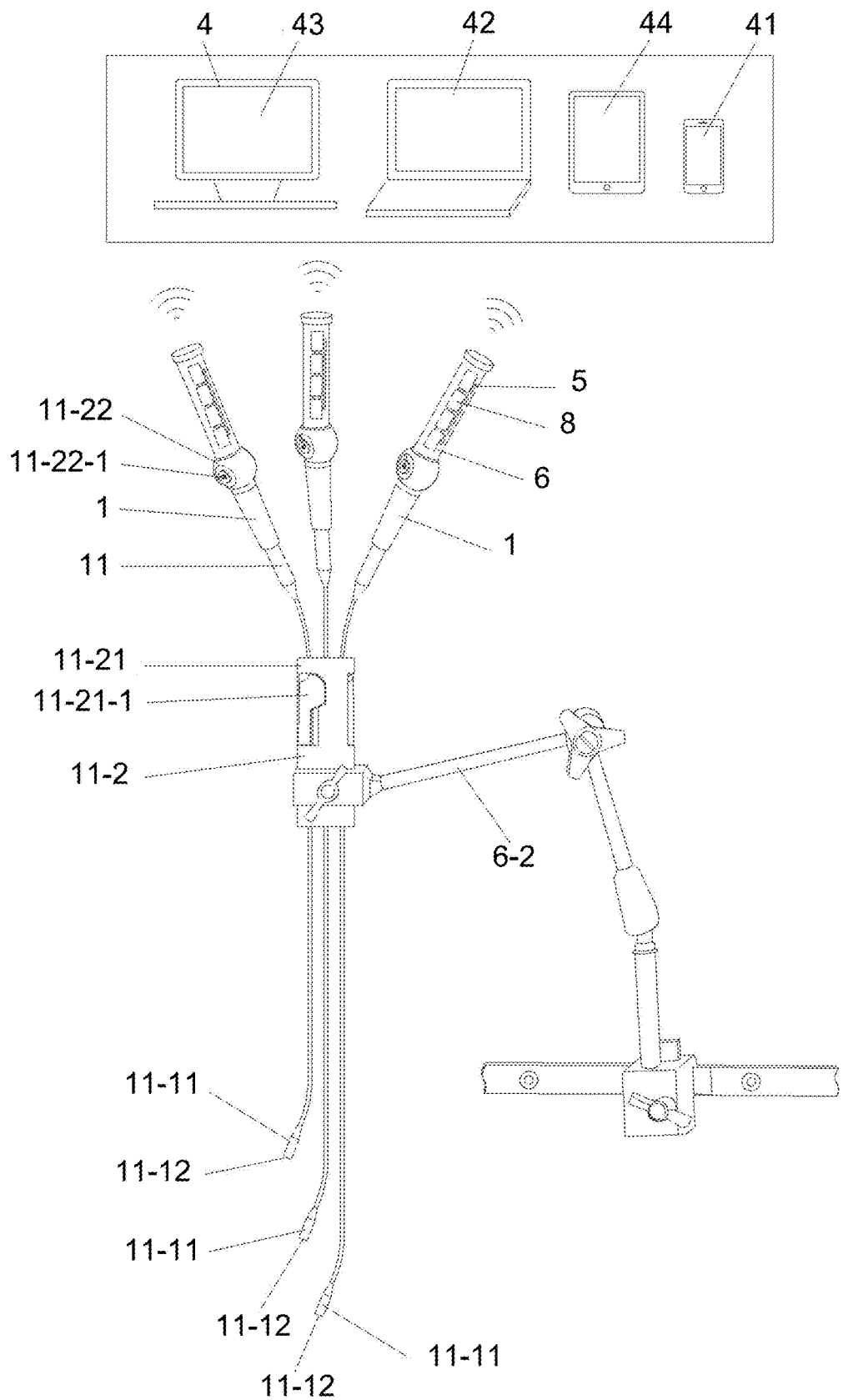
FIG. 6 is a schematic diagram illustrating that a multi-plane sleep monitoring endoscope of the present application is connected to a display system in a wireless manner.

In this embodiment, the observation system 1 is a photographing system 11, and the photographing system 11 at least includes two sets of imaging systems 11-1. There may also be more than two sets of imaging systems 11-1. Referring to FIG. 5A and FIG. 6, the applicant does not list them one by one.

The data processing and outputting system 2 and the circuit 5 are mounted in the shell 6; and the observation system 1, the data processing and outputting system 2, the lighting system 3, and the display system 4 are connected to the power system 8 through the circuit 5.

In this embodiment, after being processed by the data processing and outputting system 2, data acquired by the imaging systems 11-1 is output to the same display system 4 for displaying on split screens. The acquired data can also be output to different display systems 4 for separate displaying, and the applicant does not specifically describe it here.

A distal end of the imaging system 11-1 forms an observation end 11-12. Parts to be monitored may be observed through the observation ends 11-12. In this embodiment, the observation ends 11-12 of the two sets of imaging systems 11-1 are on two horizontal planes, so that simultaneous monitoring of two obstructive planes, particularly the velopharyngeal plane and the glossopharyngeal plane, can be realized. When there are three or more sets of imaging systems 11-1, the observation ends 11-12 of the imaging systems 11-1 may be on three or more horizontal planes to perform simultaneous monitoring of three or more obstructive planes. The applicant does not list them in detail one by one.

In this embodiment, the photographing system 11 further includes a positioning system 11-2. The positioning system 11-2 can spatially position the observation end 11-12 of the imaging system 11-1 to ensure that the observation end can be located at a proper monitored part to well adapt to individual difference of different patients.

In this embodiment, the positioning system 11-2 may be a manual positioning system. Those skilled in the art can design, as needed, different positioning systems such as an automatically controlled positioning system without departing from the protection scope of the present application.

In this embodiment, the positioning system 11-2 includes a monitored plane positioning mechanism 11-21 and a spatial state positioning mechanism 11-22. The monitored plane positioning mechanism 11-21 can adjust a distance L between horizontal planes where the two observation ends 11-12 are located by adjusting horizontal heights of the observation ends 11-12, so as to adapt to differences between different patients and between different observation planes and ensure that the observation ends 11-12 are located on obstructive planes to be monitored.

In this embodiment, the monitored plane positioning mechanism 11-21 adjusts the distance L between the planes where the observation ends 11-12 are located by means of a sliding chute. The monitored plane positioning mechanism 11-21 is provided with a locking switch 11-21-1 and a sliding chute hole 11-21-2; an insertion part 1-1 of a fiberoptic endoscope 1101 passes through the sliding chute hole 11-21-2; when the locking switch 11-21-1 is on, the insertion part 1-1 of the fiberoptic endoscope 1101 can move up and down along the sliding chute hole 11-21-2; and the observation ends 11-12 are adjusted to the planes to be monitored, such as the velopharyngeal plane and the glossopharyngeal plane. The locking switch 11-21-1 is rotated to a locked state, and the insertion part 1-1 of the fiberoptic endoscope 1101 is locked, referring to FIG. 5-1 and FIG. 5-6. The monitored plane positioning mechanism 11-21 may be fixed on a fixed object such as a sickbed through a bracket 6-2.

Those skilled in the art can design different distance adjusting methods as needed, such as rotation around an axis or a cam, without departing from the protection scope of the present application.

The spatial state positioning mechanism 11-22 is arranged at a proximal end of the fiberoptic endoscope 1101; the spatial state positioning mechanism 11-22 includes an adjusting knob 11-22-1; and the adjusting knob 11-22-1 is adjusted to adjust a spatial state of the observation end 11-12 of the fiberoptic endoscope 1101, such as radian, angle, and other different spatial position parameters of the observation end 11-12, so as to ensure a good observation field of view in the monitoring process.

The data may be output to the display system 4 in a wired or wireless manner after being processed by the data processing and outputting system 2. The data can be directly connected and output to the display system 4 in the wired manner such as through a USB cable, and can also be transmitted to the display system 4 in the wireless manner such as through Bluetooth, and WIFI, referring to FIG. 6.

In this embodiment, the imaging system 11-1 is the fiberoptic endoscope 1101. The imaging system 11-1 includes a lens 11-11, an image guide fiber 11-13, the data processing and outputting system 2, the circuit 5, and the power system 8. A distal end of the image guide fiber 11-13 of the fiberoptic endoscope 1101 forms the observation end 11-12 and is connected to the lens 11-11. The acquired data may be output to the display system 4 for displaying after being processed by the data processing and outputting system 2. The processed data can also be stored and copied.

Figure 2A:
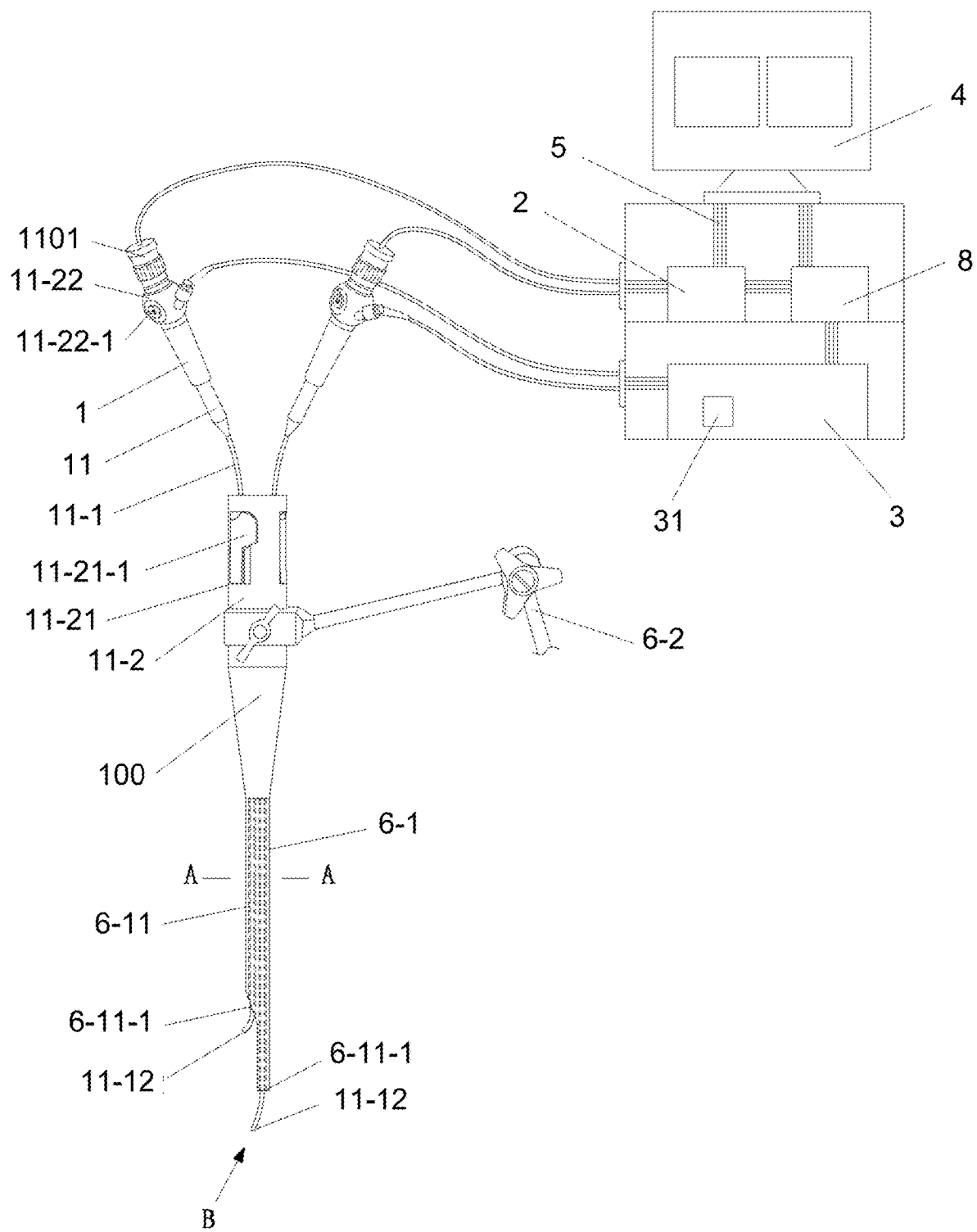
FIG. 2A is a schematic structural diagram of a multi-plane sleep monitoring endoscope of the present application including a flexible sheath.
Figure 2B:
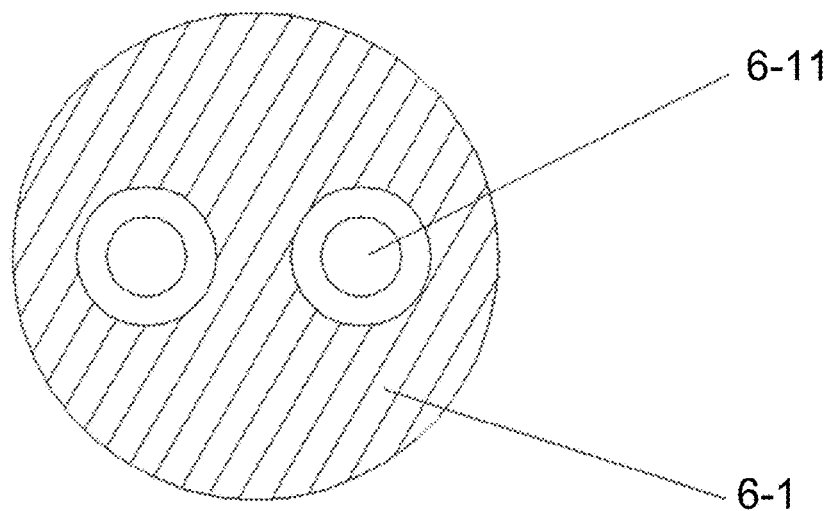
FIG. 2B is a cutaway view along A-A in FIG. 2A.
Figure 2C:
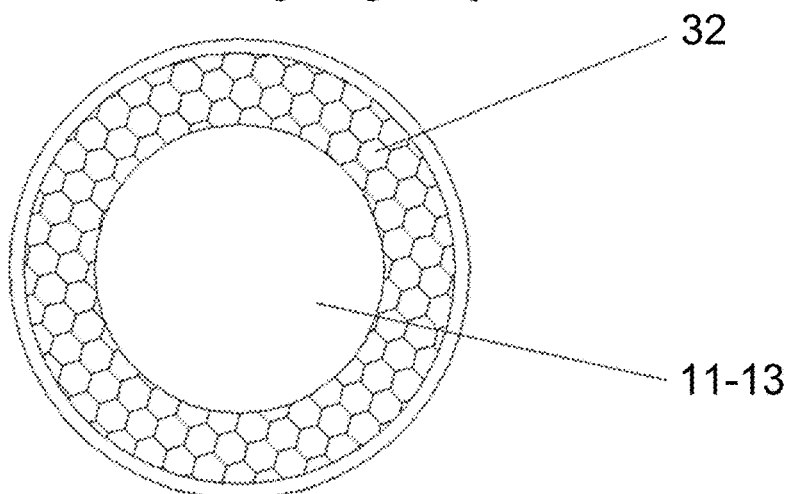
FIG. 2C is an enlarged diagram of part B in FIG. 2A.

In this embodiment, the lighting system 3 includes a light source 31 and a light guide fiber 32. The lighting system 3 provides illumination for the observation end 11-12 through the light guide fiber 32, referring to FIG. 2C.

The display system 4 may be various display devices, such as a smart phone 41, a computer 42, a liquid crystal display 43, or a tablet computer 44, referring to FIG. 6.

The multi-plane sleep monitoring endoscope 100 is made of a medical material. Due to the good biological safety performance of the medical material, the monitoring process is safer and more reliable.

During clinical use, the observation system 1, the lighting system 3, the data display system 4, and the power system 8 of the multi-plane sleep monitoring endoscope of the present application are connected; the power system 8 is turned on; the observation system 1 and the lighting system 3 are activated; the observation system 1 starts to acquire data; and the data is transmitted, via the circuit 5, to the display system 4 for displaying after being processed by the data processing and outputting system 2. After the multi-plane sleep monitoring endoscope 100 is operated normally, the locking switch 11-21-1 of the monitored plane positioning mechanism 11-21 fixed on the sickbed through the bracket 6-2 is turned on to enable the insertion part 1-1 of the first fiberoptic endoscope 1101 to pass through the sliding chute hole 11-21-2 of the monitored plane positioning mechanism 11-21, then enter, in a visible case, the upper respiratory tract along the nasal cavity, and is delivered to a plane to be monitored, such as the velopharyngeal plane and the glossopharyngeal plane. The locking switch 11-21-1 is turned off to fix the insertion part 1-1 of the first fiberoptic endoscope 1101 on the monitored plane positioning mechanism 11-21. The above actions are repeated to insert the second fiberoptic endoscope 1101 to the monitored plane and fix it, referring to FIG. 1.

Then, the spatial state of the observation end 11-12 of the fiberoptic endoscope 1101 is adjusted by adjusting the adjusting knob 11-22-1 of the spatial state positioning mechanism 11-22 arranged at a proximal end of the fiberoptic endoscope 1101, such as the radian, the angle, and other different spatial position parameters of the observation end 11-12.

Figure 7:
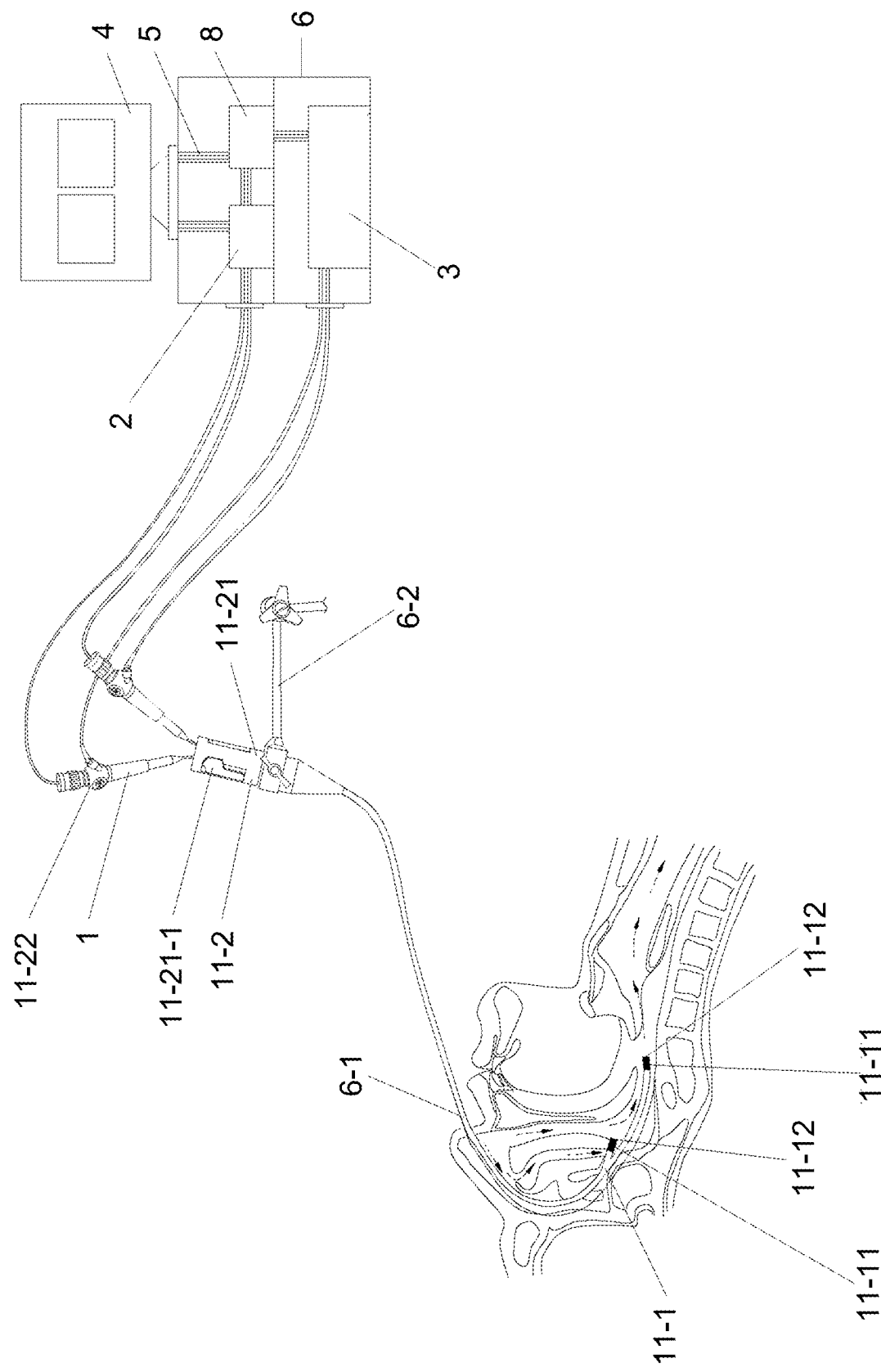
FIG. 7 is a working principle diagram of a multi-plane sleep monitoring endoscope of the present application.

After the observation ends 11-12 are all adjusted to appropriate positions and states, the sleep monitoring starts, referring to FIG. 7.

The multi-plane sleep monitoring endoscope of this embodiment has two sets of mutually independent imaging systems 11-1, so that states of two obstructive planes can be monitored at the same time. Since the imaging systems 11-1 are mutually independent, relative positions and spatial states of the observation ends 11-12 can be separately adjusted, and the flexibility is high during use.

Figure 3A:
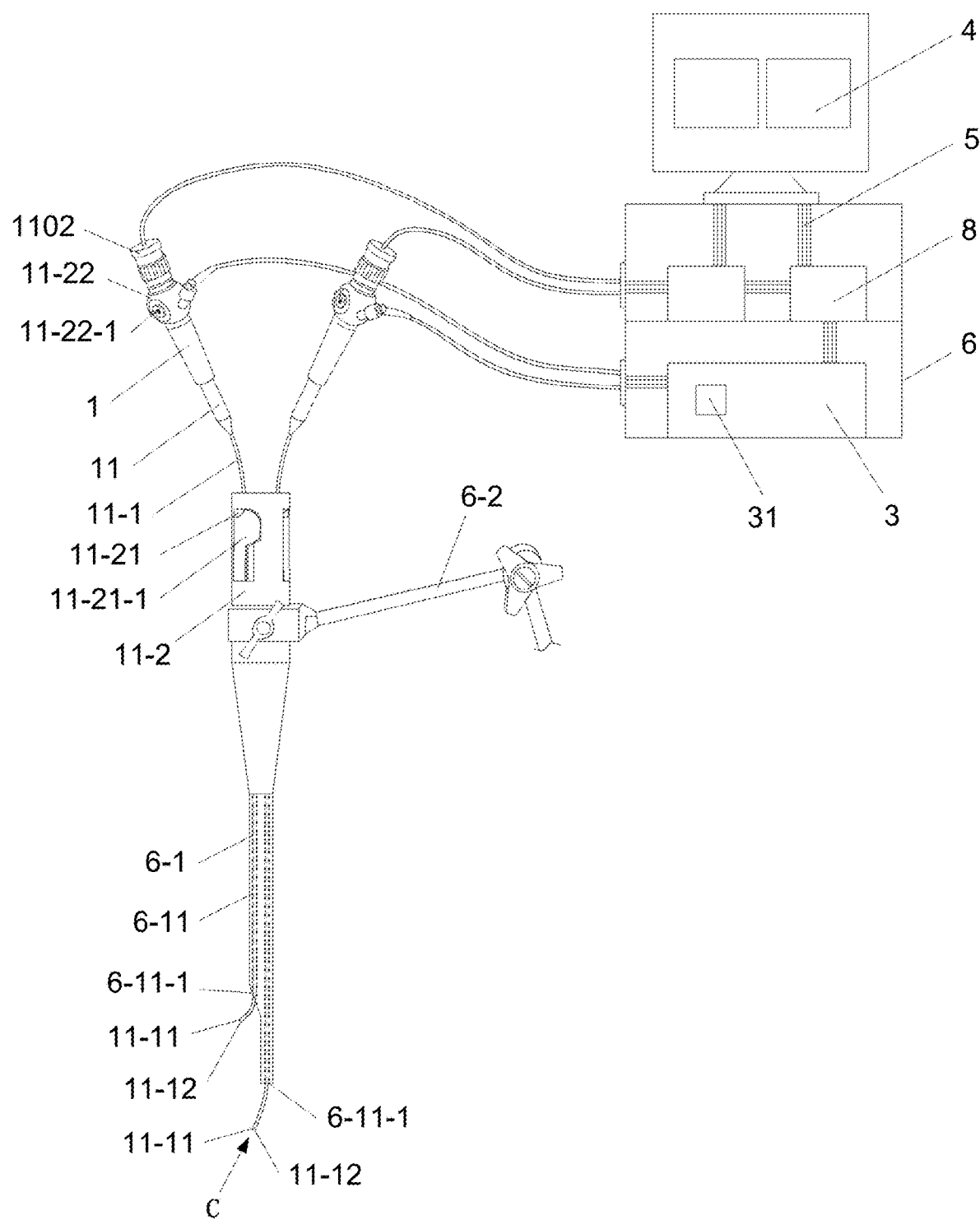
FIG. 3A is a schematic structural diagram of a multi-plane sleep monitoring endoscope of the present application including two electronic endoscopes.

Referring to FIG. 3A, when there are three sets of imaging systems 11-1 designed, the multi-plane sleep monitoring endoscope of the present application can monitor states of three obstructive planes at the same time.

Embodiment 2: Multi-plane sleep monitoring endoscope of the present application including a flexible sheath Referring to FIGS. 2A to 2C, a difference between this embodiment and Embodiment 1 is that in this embodiment, the multi-plane sleep monitoring endoscope 100 further includes a flexible sheath 6-1.

In this embodiment, the observation system 1 is delivered through the flexible sheath 6-1. The soft flexible sheath 6-1 makes a patient feel more comfortable in the delivery process.

In this embodiment, the flexible sheath 6-1 and the monitored plane positioning mechanism 11-21 are manufactured into a whole. In practical use, those skilled in the art can also design the flexible sheath 6-1 into a detachable structure without departing from the protection scope of the present application.

In this embodiment, the flexible sheath 6-1 includes two working channels 6-11, and channel outlet ends 6-11-1 of the working channels 6-11 are not on the same horizontal plane.

During clinical use, the insertion parts 1-1 of the fiberoptic endoscopes 1101 are respectively inserted into the sliding chute hole 11-21-2 of the monitored plane positioning mechanism 11-21; and when the observation ends 11-12 of the two sets of imaging systems 11-1 are respectively exposed from the channel outlets 6-11-1 of the working channels 6-11, the locking switch 11-21-1 is turned off to fix the insertion parts 1-1.

The power system 8 is turned on, and the multi-plane sleep monitoring endoscope of the present application starts to work; the flexible sheath 6-1 is then inserted into the respiratory tract via the nasal cavity and delivered to a position near the plane to be monitored; and the bracket 6-2 is used to fix the monitored plane positioning mechanism 11-21 on the sickbed. The locking switch 11-21-1 is turned on, and the observation ends 11-12 are respectively adjusted to suitable monitored plane heights; the locking switch 11-21-1 is turned off to lock the insertion parts 1-1; and the spatial state of the observation end 11-12 of the fiberoptic endoscope 1101 is adjusted to an appropriate state by adjusting the adjusting knob 11-22-1 of the spatial state positioning mechanism 11-22 arranged at the proximal end of the fiberoptic endoscope 1101, so as to start the sleep monitoring, referring to FIG. 7.

In this embodiment, the flexible sheath 6-1 includes a plurality of working channels 6-11, so that the multiple sets of imaging systems 11-1 may be simultaneously arranged in one flexible sheath 6-1, and the delivery process can be finished at one time; furthermore, when the monitored planes and the spatial states are adjusted, the insertion parts 1-1 move back and forth in the flexible sheath 6-1, and the adjustment will not make the patient feel uncomfortable. Compared to Embodiment 1, the clinical use of the multi-plane sleep monitoring endoscope of this embodiment makes the patient feel more comfortable and is more convenient.

Figure 3B:
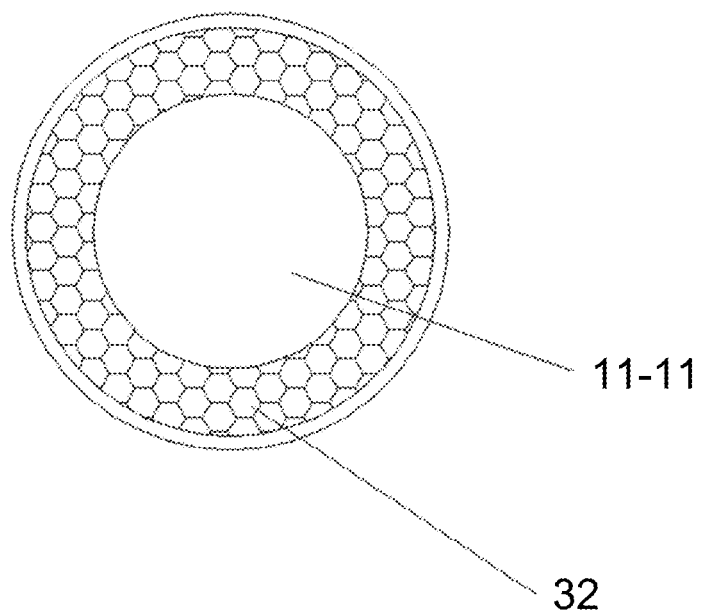
FIG. 3B is an enlarged diagram of part C in FIG. 3A.

Embodiment 3: Multi-plane sleep monitoring endoscope of the present application including an electronic endoscope Referring to FIG. 3A and FIG. 3B, a difference between this embodiment and Embodiment 2 is that in this embodiment, the imaging system 11-1 is an electronic endoscope 1102.

The lens 11-11 of the electronic endoscope 1102 is arranged at the distal end of the insertion part 1-1 of the electronic endoscope 1102. The distal end of the lens 11-11 forms the observation end 11-12. The light guide fiber 32 guides illuminating light emitted by the light source 31 to the observation end 11-12 to provide illumination for the lens 11-11.

In this embodiment, since the lens 11-11 is arranged at the distal end of the insertion part 1-1 of the electronic endoscope 1102, the lens 11-11 can directly acquire image data, without image transmission by the image guide fiber 11-13, and the image is clearer and more real. After the image data acquired by the electronic endoscope is converted into electric signals, the electric signals are transmitted through a cable. Therefore, only the lens 11-11 at an end part needs to be ensured at a certain size, and the cable may be very small in size. Therefore, compared with the fiberoptic endoscope 1101, the electronic endoscope 1102 has a smaller size and makes the patient feel more comfortable.

Figure 4A:
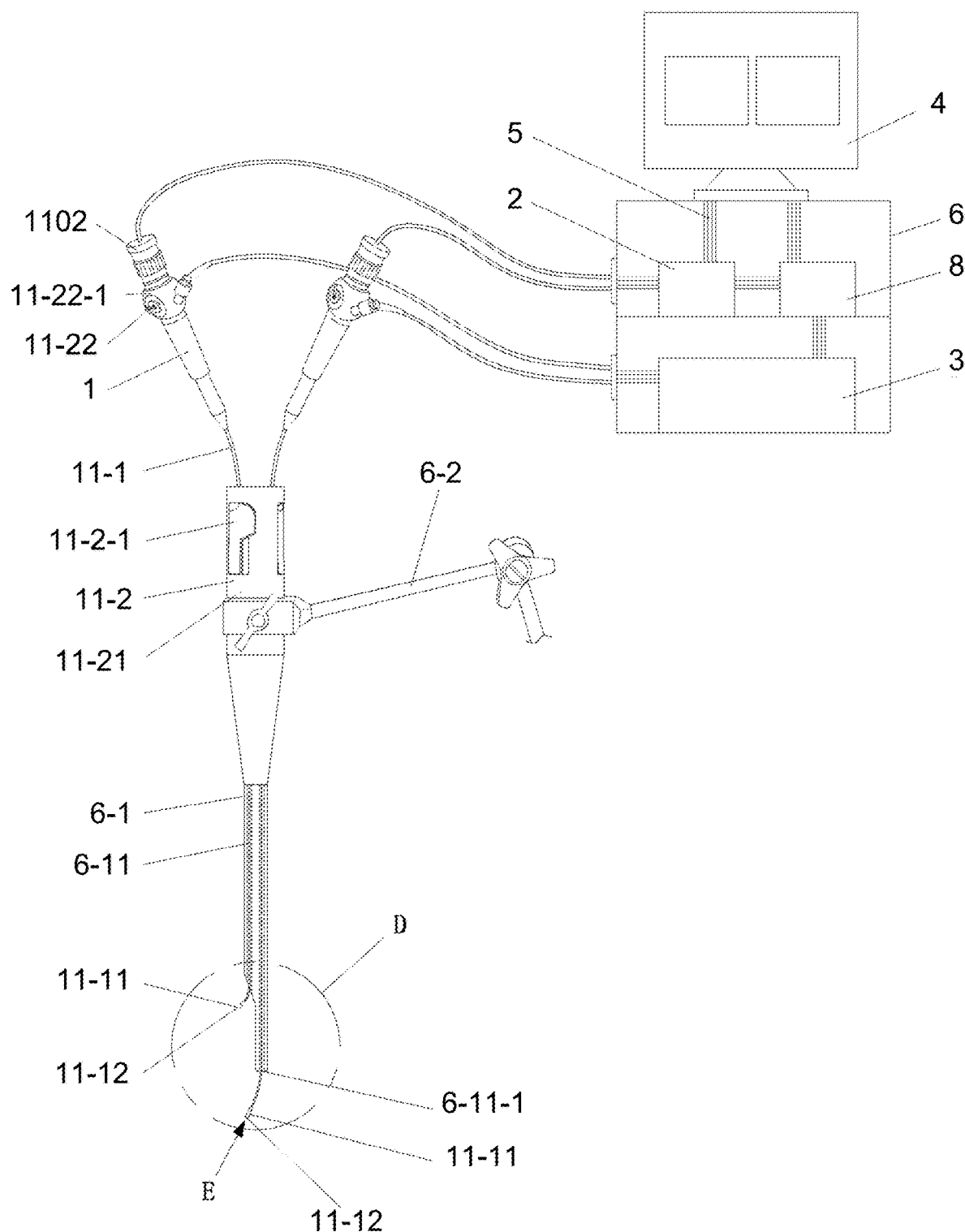
FIG. 4A is a schematic structural diagram of a multi-plane sleep monitoring endoscope of the present application including an LED light source.
Figure 4B:
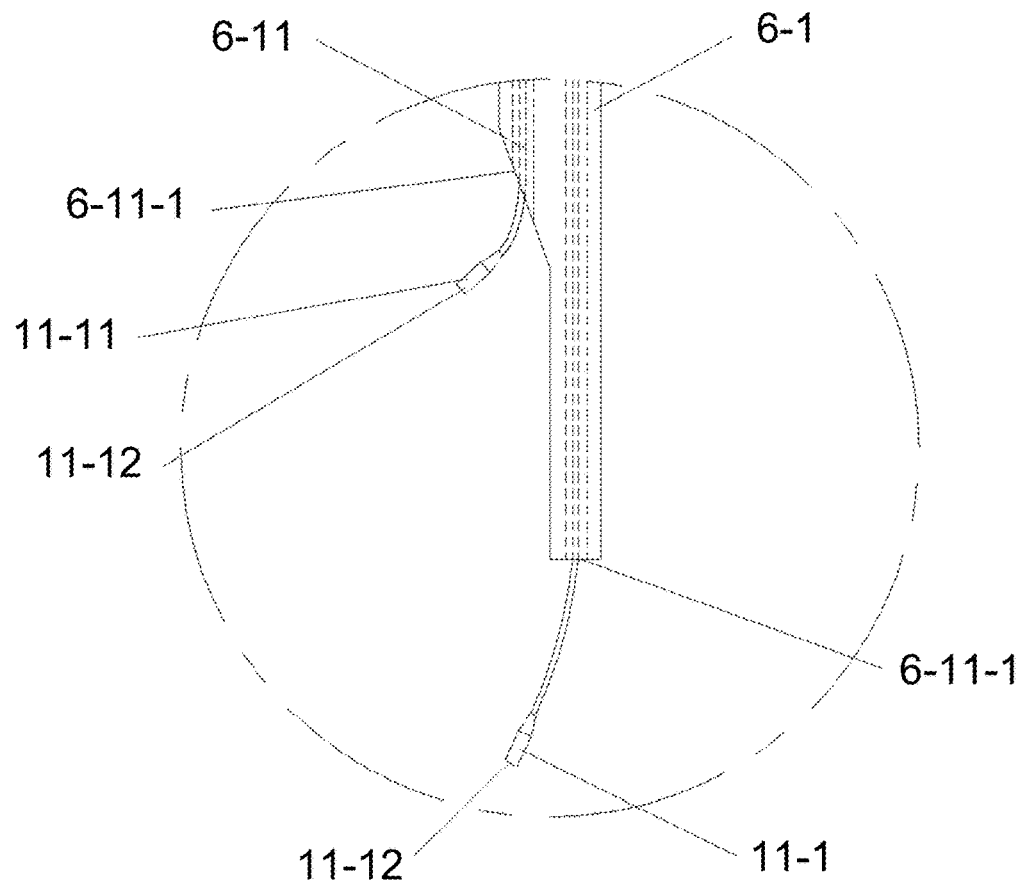
FIG. 4B is an enlarged diagram of part D in FIG. 4A.
Figure 4C:
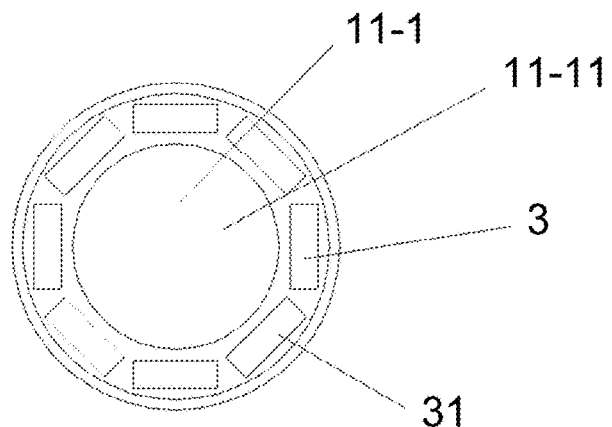
FIG. 4C is an enlarged diagram of part E in FIG. 4A.

Embodiment 4: Multi-plane sleep monitoring endoscope of the present application including an LED light source Referring to FIGS. 4A to 4C, compared to Embodiment 3, in this embodiment, the lighting system 3 is directly arranged around the lens 11-11, so that the illumination effect is better than that of Embodiment 3.

In this embodiment, the lighting system 3 adopts the LED light source. Compared with an ordinary illumination light source, the LED light source has the characteristics of small volume, high light-emitting efficiency, high light directivity, and the like. Particularly in terms of safety, the LED light source has incomparable advantages to the ordinary light source. First of all, the LED light source is supplied with low-voltage (DC) power, and a power supply voltage is only 6 to 24 V. Secondly, no mercury is added into the LED light source, which will not cause poisoning and other harm to the human body. In addition, more importantly, the LED light source is a cold light source, which will not seriously generate heat in a working process. The LED light source can be safely touched and will not cause accidental high-temperature scald to the human body. Meanwhile, the LED light source generates heat appropriately, so that a certain heat balance can be achieved around the lens, and a certain anti-fog effect is realized, which makes an observation process clearer and stabler.

Figure 5H:
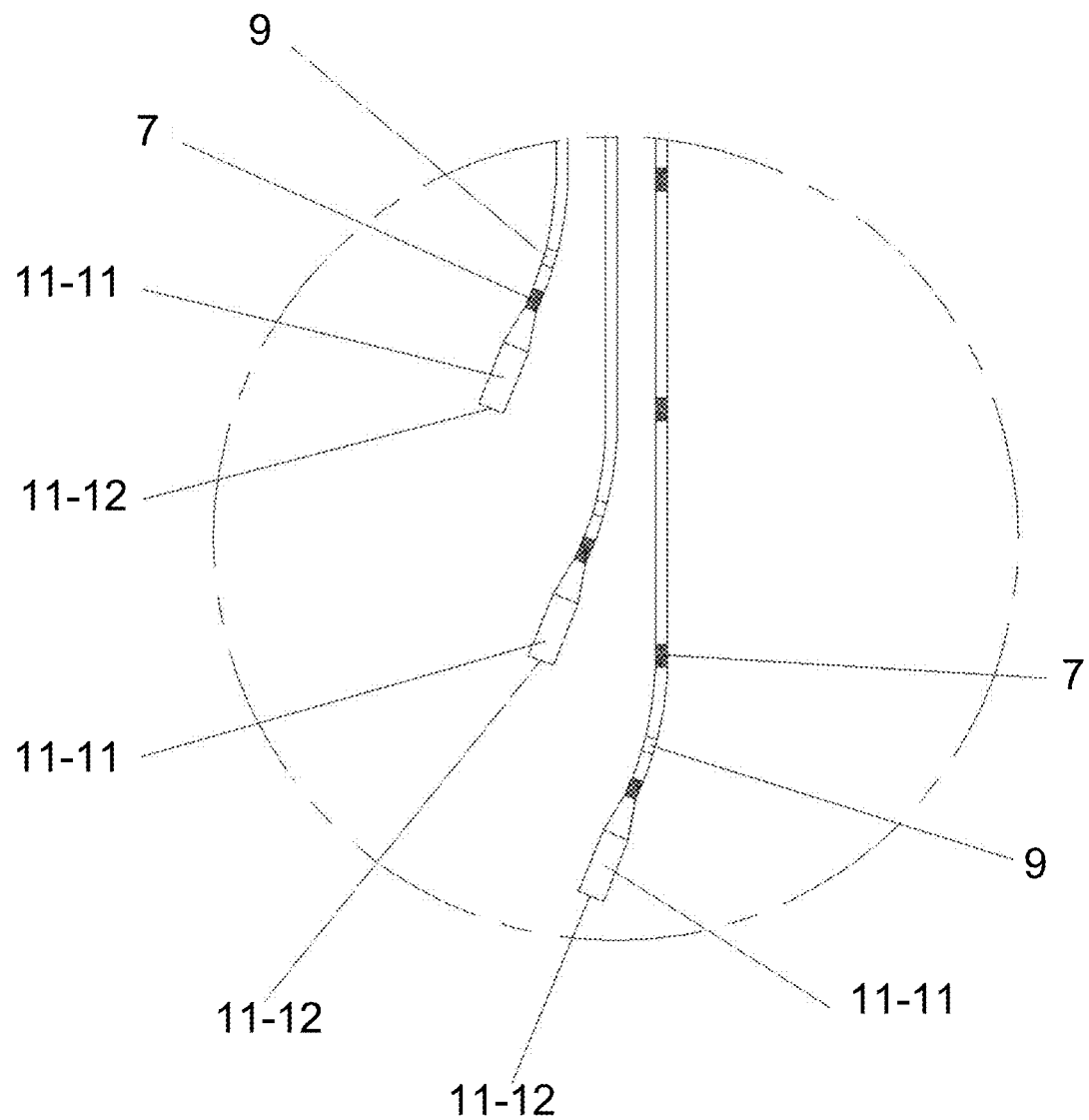
FIG. 5H is an enlarged diagram of part F in FIG. 5A.

In addition, a pressure sensor 7 or a flow velocity sensor 9 may also be arranged near the observation end 11-12, referring to FIG. 5A and FIG. 5H. The pressure sensor 7 can measure a pressure of breathing near the observation end 11-12, and the flow velocity sensor 9 can measure a flow rate of a breathing air flow near the observation end 11-12. The pressure data measured by the pressure sensor 7 and the flow rate data of the air flow measured by the flow velocity sensor 9 can also be output to the display system 4 for real-time displaying, recording, and storage, referring to FIG. 5A.

Embodiment 5: Multi-plane sleep monitoring endoscope of the present application including a body surface fixing mechanism Referring to FIG. 8 and FIG. 9, a difference between this embodiment and Embodiment 4 is that in this embodiment, the positioning system 11-2 further includes a body surface fixing mechanism 11-23.

The body surface fixing mechanism 11-23 can fix the imaging system 11-1 on a human body. Even if the patient's body position changes during sleep, it will not cause the imaging system 11-1 to move, and will not affect the photographing effect of the lens 11-11.

Figure 8:
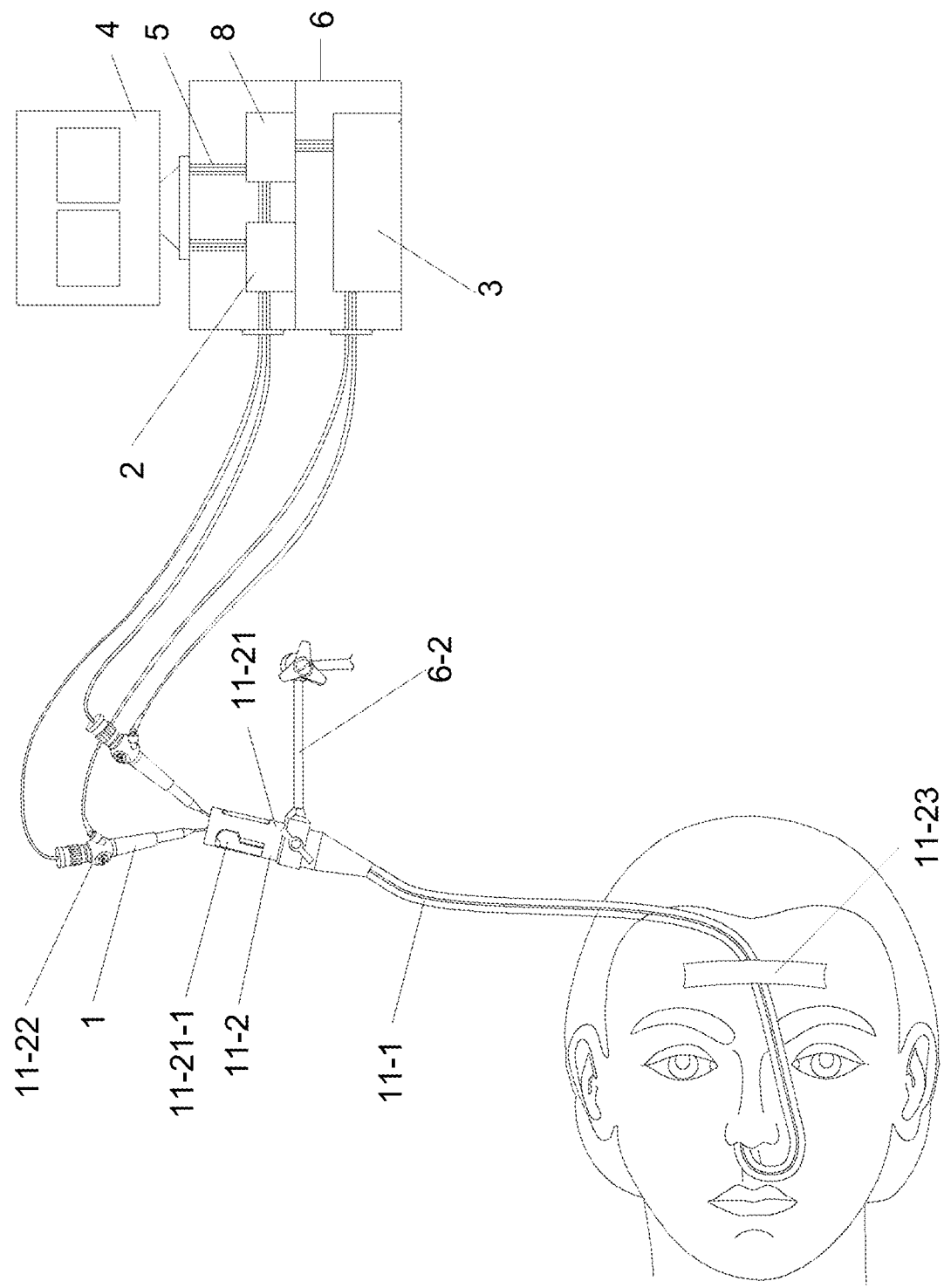
FIG. 8 is a working principle diagram illustrating that a multi-plane sleep monitoring endoscope of the present application including two sets of separately disposed imaging systems is adhered and fixed on the forehead by a body surface fixing mechanism.
Figure 9:
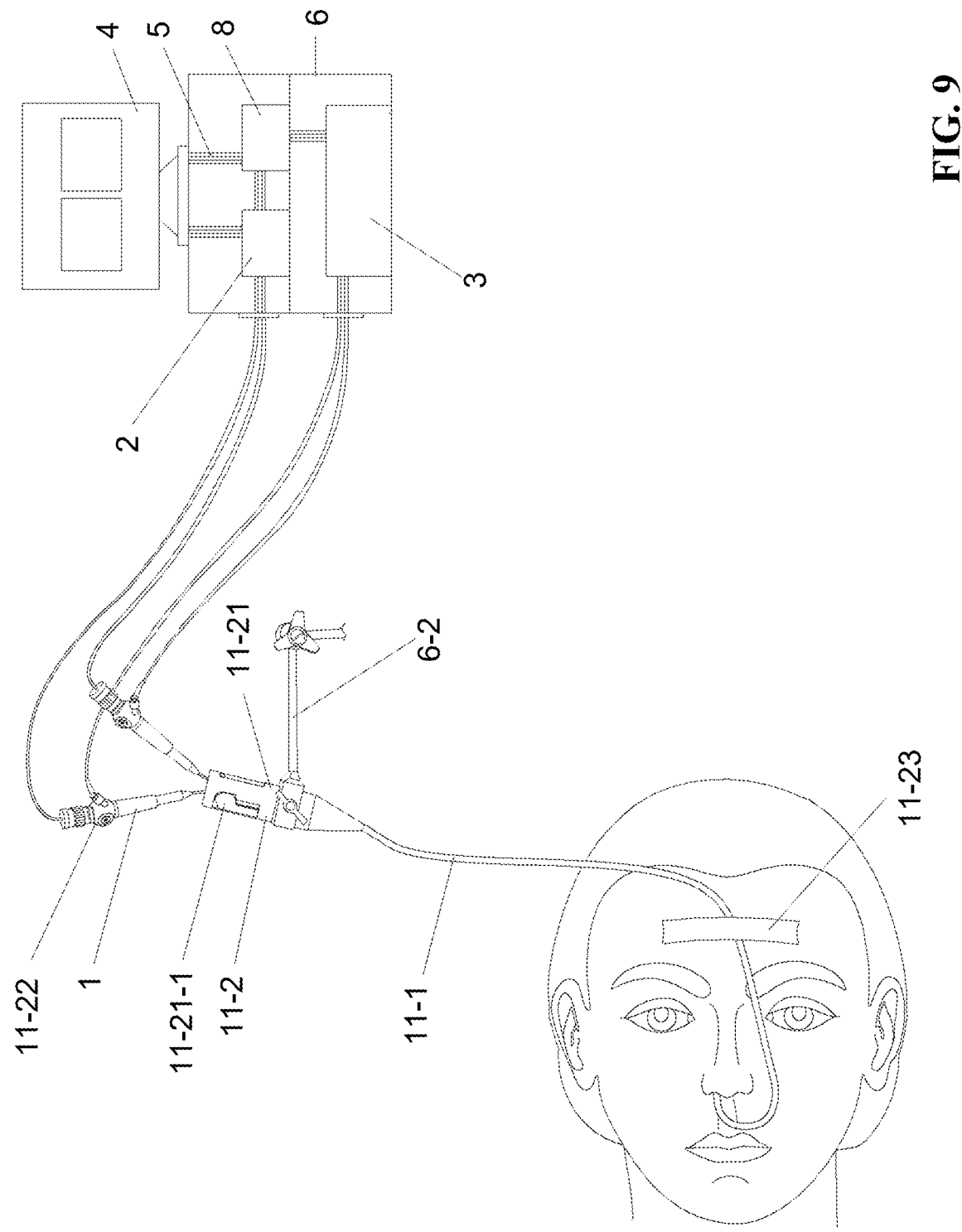
FIG. 9 is a working principle diagram illustrating that a multi-plane sleep monitoring endoscope of the present application including imaging systems combined in one sheath is adhered and fixed on the forehead.
Figure 10:
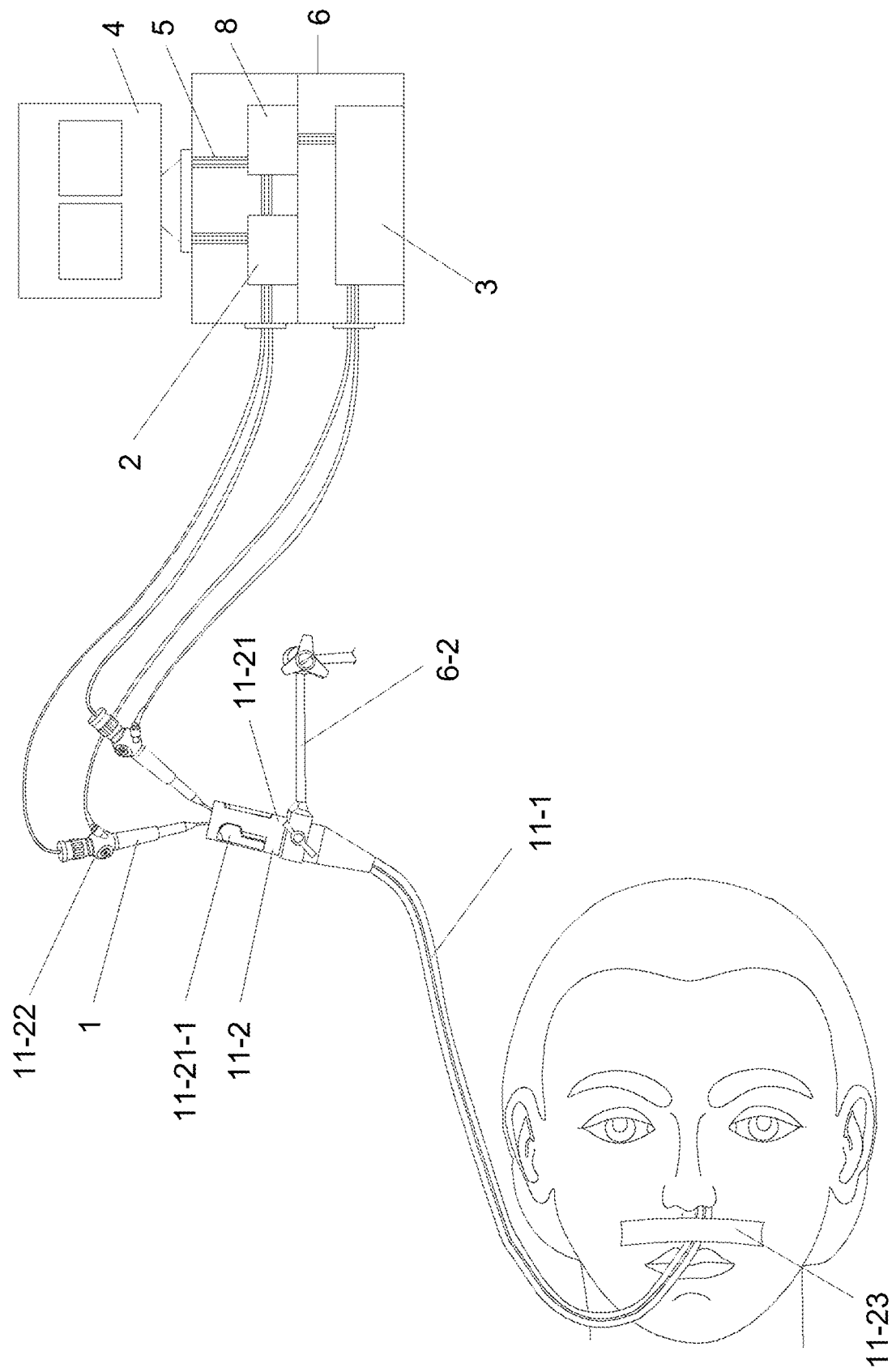
FIG. 10 is a working principle diagram illustrating that the multi-plane sleep monitoring endoscope of the present application in FIG. 8 is adhered and fixed on the philtrum.
Figure 11:
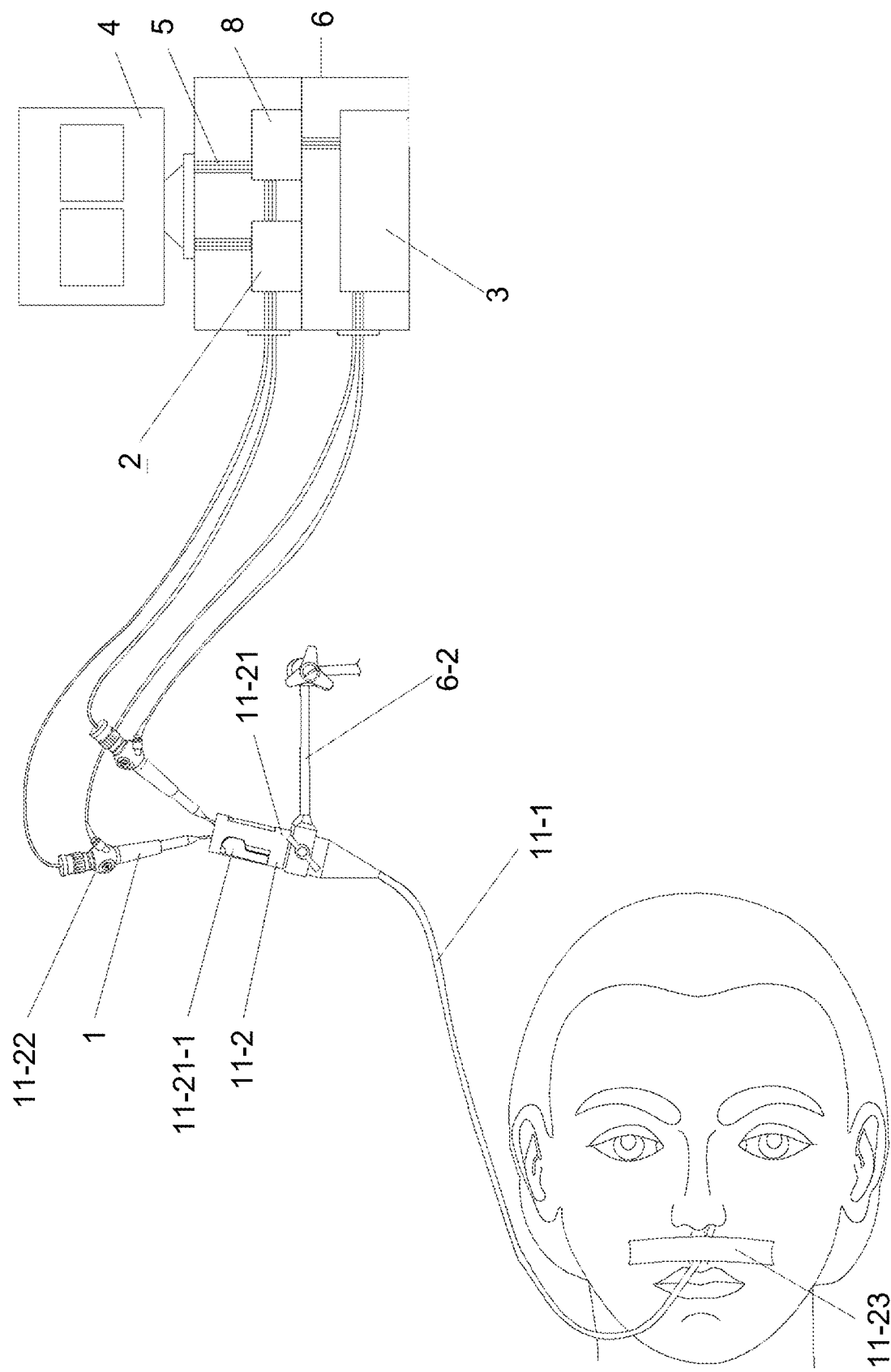
FIG. 11 is a working principle diagram illustrating that the multi-plane sleep monitoring endoscope of the present application in FIG. 9 is adhered and fixed on the philtrum.

Referring to FIG. 8 and FIG. 9, in this embodiment, the body surface fixing mechanism 11-23 fixes the imaging system 11-1 on the forehead of the human body by means of adhering. In practical applications, the body surface fixing mechanism 11-23 can also fix the imaging system 11-1 on various parts of the human body, such as the mandible, the philtrum, and the cheek, by other means such as strapping and a mesh bag, referring to FIG. 10 and FIG. 11.

In clinical use, after the monitored planes are adjusted through the monitored plane positioning mechanism 11-21, the spatial state positioning mechanism 11-22 is adjusted to an appropriate spatial state and fixed in this state and then is adhered to the forehead of the patient through the body surface fixing mechanism 11-23; and the distal end of the imaging system 11-1 is fixed on the forehead of the patient, and the sleep monitoring is started.

In this embodiment, since the body surface fixing mechanism 11-23 fixes the distal end of the imaging system 11-1 on the body surface of the human body, the insertion part 1-1 entering the human body will not move relative to the human body even if the body position changes during the sleep, thereby better guaranteeing the observation plane and the spatial position of the lens 11-11.

Figure 12A:
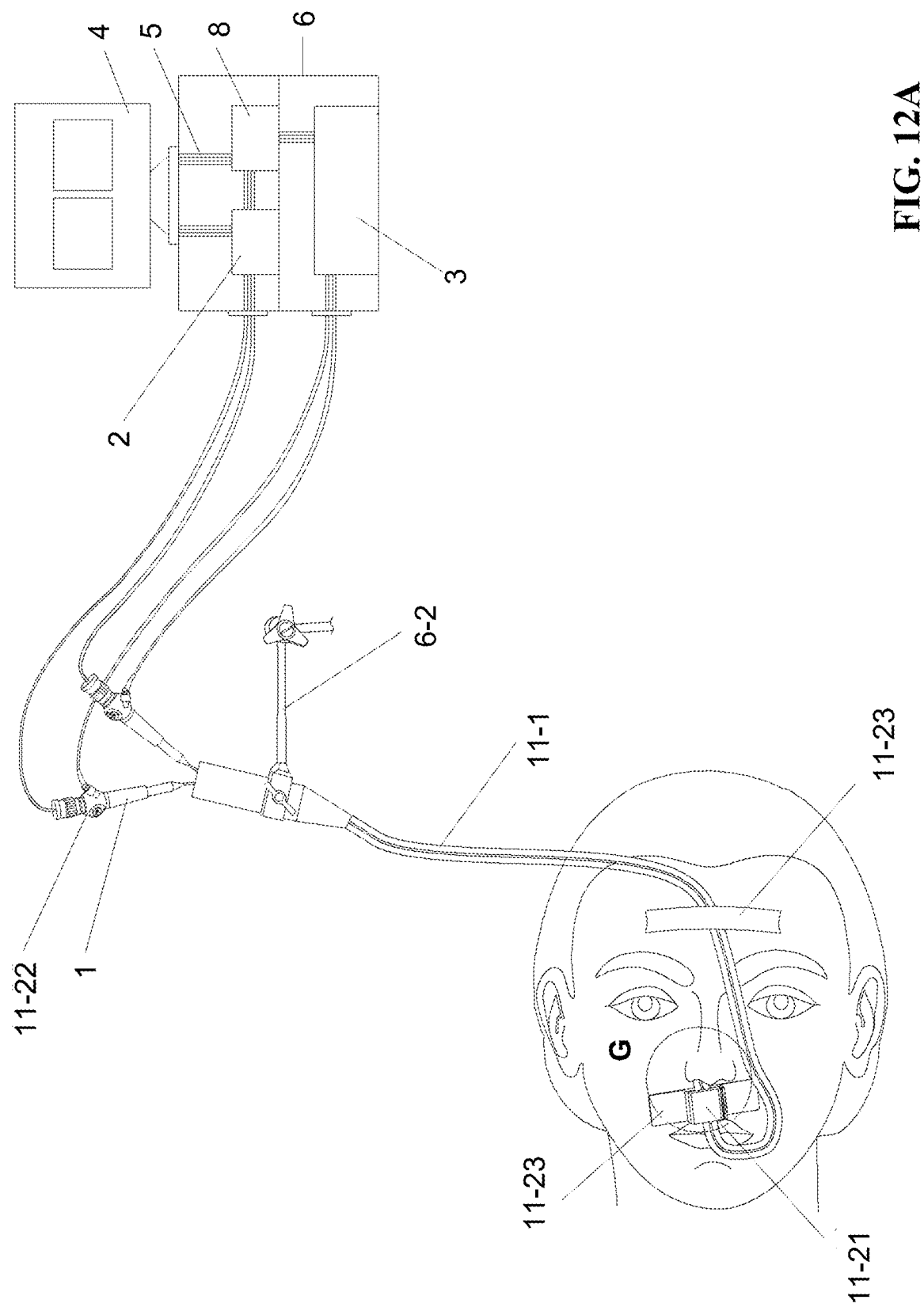
FIG. 12A is a working principle diagram of a multi-plane sleep monitoring endoscope of the present application in which a monitored plane positioning mechanism and a body surface fixing mechanism are disposed together.
Figure 12B:
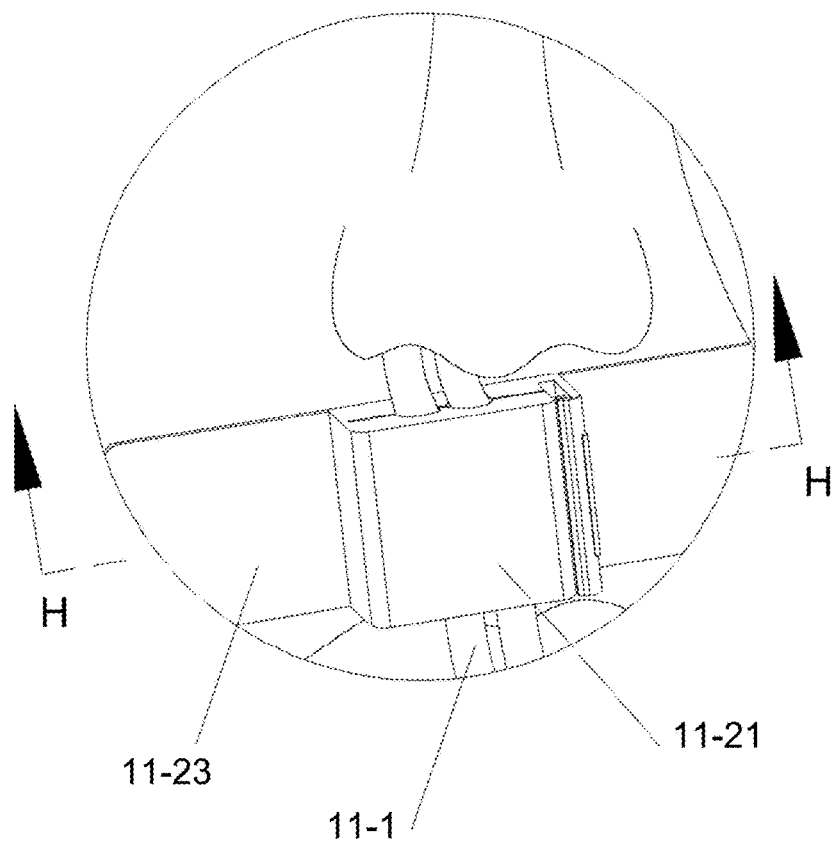
FIG. 12B is an enlarged diagram of part G in FIG. 12A.
Figure 12C:
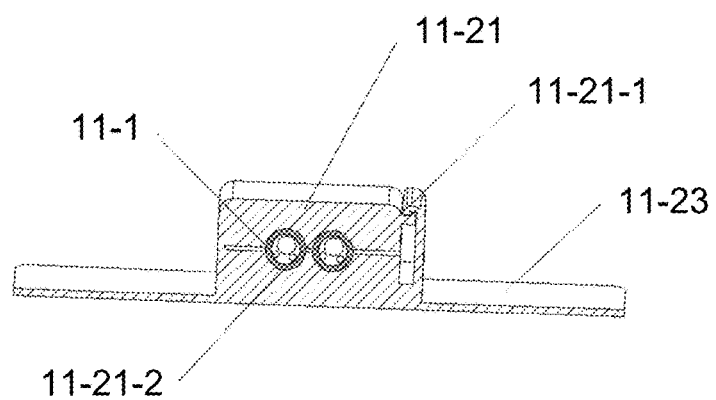
FIG. 12C is a cutaway view along H-H of FIG. 12B.

In this embodiment, the monitored plane positioning mechanism 11-21 and the spatial state positioning mechanism 11-22 are provided separately from the body surface fixing mechanism 11-23. In practical applications, to simplify the structure, the monitored plane positioning mechanism 11-21 and/or the spatial state positioning mechanism 11-22 and the body surface fixing mechanism 11-23 are arranged together to facilitate the operations of the two steps of state adjustment and body surface fixing, referring to FIGS. 12A to 12C.

The monitored plane positioning mechanism 11-21 is arranged on the body surface fixing mechanism 11-23, and after the distal end of the imaging system 11-1 is inserted into the sliding chute hole 11-21-2 of the monitored plane positioning mechanism 11-21, the locking switch 11-21-1 is pressed to fix the imaging system 11-1.

During actual application, a person skilled in the art may further design other various combination structures, which are not described by using a specific example by the applicant, and do not depart from the protection scope of this application.

It should be noted that the structure disclosed and described in this specification may be replaced with another structure with the same effect. In addition, the embodiments described in the present application are not the only structure of implementing the present application. Although exemplary embodiments of the present application have been introduced and described in this specification, it should be understood by a person skilled in the art that the embodiments are merely described by way of example, and a person skilled in the art may make various changes, improvements, and replacements without departing from the present application. Therefore, the protection scope of the present application should be defined in accordance with the spirit and scope of the claims appended to the present application.

What is claimed is:

1. A multi-plane sleep monitoring endoscope, comprising:
an observation system, a data processing and outputting system, a lighting system, a display system, a circuit, a shell, and a power system;
wherein:
the observation system is a photographing system that comprises at least two imaging systems, the photographing system comprises a positioning system that includes a monitored plane positioning mechanism, wherein the monitored plane positioning mechanism is configured to be fixed to a patient bed via a bracket;
the data processing and outputting system and the circuit are mounted in the shell;
the observation system, the data processing and outputting system, the lighting system, and the display system are connected to the power system through the circuit;
the observation system is provided with a pressure sensor near an observation end of the multi-plane sleep monitoring endoscope, proximate to a patient, for measuring breathing pressure of the patient; and
the display system is configured to display, in real-time, the measured breathing pressure of the patient that is measured by the pressure sensor.

2. The multi-plane sleep monitoring endoscope according to claim 1, wherein:
the at least two imaging systems include a first imaging system having a lens, the data processing and outputting system, the circuit, and the power system; and
data acquired by the lens is configured to be output to the display system after being processed by the data processing and outputting system.

3. The multi-plane sleep monitoring endoscope according to claim 2, wherein the first imaging system is a fiberoptic endoscope.

4. The multi-plane sleep monitoring endoscope according to claim 2, wherein the first imaging system is an electronic endoscope.

5. The multi-plane sleep monitoring endoscope according to claim 4, wherein a distal end of the lens of the electronic endoscope forms an observation end; data acquired by the lens is output to the display system after being processed by the data processing and outputting system; the lighting system comprises a light source and a light guide fiber; and the light guide fiber guides illuminating light emitted by the light source to the observation end to provide illumination for the lens.

6. The multi-plane sleep monitoring endoscope according to claim 4, wherein the lighting system is arranged around the lens of the electronic endoscope to provide illumination for the lens.

7. The multi-plane sleep monitoring endoscope according to claim 6, wherein the lighting system is a light-emitting diode light source.

8. The multi-plane sleep monitoring endoscope according to claim 2, wherein data processed by the data processing and outputting system is configured to be output to the display system in a wired or wireless manner.

9. The multi-plane sleep monitoring endoscope according to claim 1, wherein the at least two imaging systems include a first imaging system having a first distal end that forms a first observation end and a second imaging system having a second distal end that forms a second observation end; and the first observation end and the second observation end are not on the same horizontal plane.

10. The multi-plane sleep monitoring endoscope according to claim 9, wherein the positioning system is configured to position the first observation end of the first imaging system and the second observation end of the second imaging system.

11. The multi-plane sleep monitoring endoscope according to claim 10, wherein the positioning system further includes a spatial state positioning mechanism.

12. The multi-plane sleep monitoring endoscope according to claim 11, wherein a distance L between planes where the first observation end of the first imaging system and the second observation end of the second imaging system are located is adjusted through the monitored plane positioning mechanism.

13. The multi-plane sleep monitoring endoscope according to claim 12, wherein the monitored plane positioning mechanism adjusts, by means of a sliding chute, rotation around an axis, or a cam, the distance L between the planes where the observation ends are located.

14. The multi-plane sleep monitoring endoscope according to claim 11, wherein the spatial state positioning mechanism is configured to adjust a spatial state of the observation end.

15. The multi-plane sleep monitoring endoscope according to claim 1, wherein the display system is one of a smart phone, a computer, a liquid crystal display, and a tablet computer.

16. The multi-plane sleep monitoring endoscope according to claim 1, wherein the multi-plane sleep monitoring endoscope is made of a biological compatible material.

17. The multi-plane sleep monitoring endoscope according to claim 1, wherein the observation system is delivered through a flexible sheath.

18. The multi-plane sleep monitoring endoscope according to claim 17, wherein the flexible sheath comprises at least two working channels, and channel outlet ends of the at least two working channels are not on the same horizontal plane.

* * * * *